(12) United States Patent
Xi et al.

(10) Patent No.: US 10,913,765 B2
(45) Date of Patent: *Feb. 9, 2021

(54) LIVER SPECIFIC DELIVERY-BASED GEMCITABINE PRODRUG NUCLEOSIDE CYCLIC PHOSPHATE COMPOUND, AND APPLICATION THEREOF

(71) Applicant: ZHEJIANG PALO ALTO PHARMACEUTICALS, INC., Quzhou (CN)

(72) Inventors: Zhijian Xi, Quzhou (CN); Huaqiang Xu, Quzhou (CN); Chunping Lu, Quzhou (CN); Zhongshan Wu, Quzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/906,141

(22) Filed: Jun. 19, 2020

(65) Prior Publication Data
US 2020/0317712 A1    Oct. 8, 2020

Related U.S. Application Data

(63) Continuation of application No. PCT/CN2018/122821, filed on Dec. 21, 2018.

(30) Foreign Application Priority Data

Dec. 22, 2017 (CN) .......................... 2017 1 1407838

(51) Int. Cl.
C07H 19/11    (2006.01)
A61P 35/00    (2006.01)

(52) U.S. Cl.
CPC .............. C07H 19/11 (2013.01); A61P 35/00 (2018.01)

(58) Field of Classification Search
None
See application file for complete search history.

(56) References Cited

U.S. PATENT DOCUMENTS

| 10,117,888 | B2 | 11/2018 | Griffith et al. | |
| 10,668,090 | B2 * | 6/2020 | Xi | ........................ A61K 31/675 |
| 2010/0305060 | A1 | 12/2010 | Hecker et al. | |
| 2019/0192547 | A1 | 6/2019 | Li | |

FOREIGN PATENT DOCUMENTS

| CN | 1711278 | A | 12/2005 | |
| CN | 1733779 | A | 2/2006 | |
| CN | 101475594 | A | 7/2009 | |
| CN | 104211742 | A | 12/2014 | |
| WO | WO-2009053654 | A2 * | 4/2009 | .............. C07H 19/10 |

OTHER PUBLICATIONS

Internation Search Report of PCT/CN2018/122821, dated Mar. 20, 2019.

* cited by examiner

Primary Examiner — Traviss C McIntosh, III
(74) Attorney, Agent, or Firm — W&K IP

(57) ABSTRACT

Provided are a liver specific delivery (LSD)-based anticancer prodrug nucleoside cyclic phosphate compound and an application thereof, and in particular, a compound represented by formula (I) as well as isomers, pharmaceutically acceptable salts, hydrates, and solvates thereof, and corresponding pharmaceutical compositions. Also provided is an application of the compound alone or in combination with other anticancer drugs in anticancer area, particularly the treatment of hepatocellular carcinoma (HHC).

(I)

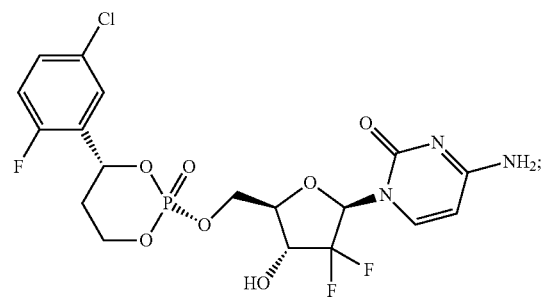

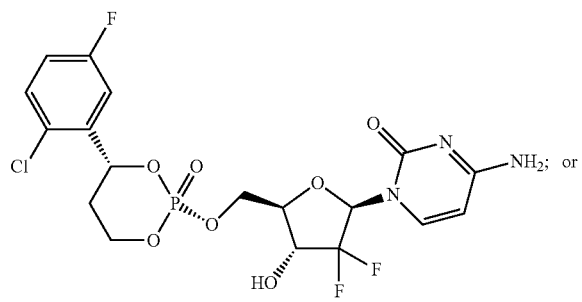

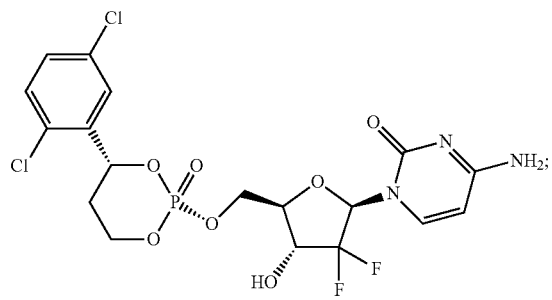

3 Claims, No Drawings

LIVER SPECIFIC DELIVERY-BASED GEMCITABINE PRODRUG NUCLEOSIDE CYCLIC PHOSPHATE COMPOUND, AND APPLICATION THEREOF

CROSS-REFERENCE TO RELATED APPLICATIONS

The present disclosure is a continuation application of International Application No. PCT/CN2018/122821 filed Dec. 21, 2018, and claims priority to Chinese Application No. 20171140783&2 filed on Dec. 22, 2017, which are incorporated herein by reference.

TECHNICAL FIELD

The present disclosure relates to a liver specific delivery (LSD)-based anti-cancer prodrug nucleoside cyclic phosphate compound, or an optical isomer, a hydrate, a solvate, a pharmaceutically acceptable salt and a pharmaceutical composition thereof, and preparation and use thereof.

BACKGROUND ART

Liver cancer is a primary malignant tumor occurring in the liver, and is commonly seen in patients suffering from liver cirrhosis or liver fibrosis. According to WHO statistics, the number of people dying from liver cancer is more than 700 thousands every year worldwide, and the liver cancer is the second deadly cancer. Viral hepatitis is an important inducement causing liver cancer, and Asia and Africa are regions with the highest incidence of liver cancer due to prevalence of viral hepatitis type b and c. At present, treatment for liver cancer is a multidisciplinary comprehensive treatment, and mainly includes operations, local ablation treatment, interventional therapy, radiotherapy, chemotherapy, targeted therapy and so on.

At present, nucleoside chemotherapeutic drugs for treatment of liver cancer are limited, only fluorouracil is used for second-line treatment, and gemcitabine is not suitable for solid tumors such as liver cancer. Gemcitabine needs to be converted into a monophosphate form through the action of phosphokinase in cells, and then is further phosphorylated into a triphosphate form, so that the DNA replication of tumor cells can be inhibited, and due to the lack of deoxycytidine kinase in solid tumors, active ingredients in the solid tumors are few, and the treatment effect is poor.

Utilizing liver specific delivery technology, the present disclosure bypasses the phosphorylation step of kinase, and successfully improves the concentration of active ingredients in the liver.

The cyclic phosphate modified gemcitabine prodrug is metabolized by CYP3A enzyme in the liver, and does not need phosphokinase to generate monophosphate compound.

Specifically, nucleoside chemotherapeutic drugs need to be converted into triphosphate form by a series of actions of phosphokinase in cells, so that the DNA replication of tumor cells can be inhibited. The precursor structure of cyclic phosphate (4-aryl-2-oxo-1,3,2-dioxaphosphorinane) has very good liver specific delivery performance, which mechanism is very clear, i.e., 4-aryl substitution position is specifically catalyzed by CYP3A in cytochrome P450 isoenzyme family in hepatocytes to generate hydroxyl, then ring-opening is carried out to generate phosphate intermediate with negative charge, which substance is not easy to penetrate through the cell membrane, and thus exists in the cell, and under the catalysis of phosphodiesterase, nucleotide monophosphate compound is generated through hydrolysis and β-elimination reaction. Nucleotide triphosphate compound with biological activity is generated continuously under the action of nucleotide kinase, and meanwhile, metabolic byproduct aryl vinyl ketone can be eliminated through 1,4-addition reaction with glutathione which is rich in hepatocytes and can resist oxidation and free radicals, and no report has been made that this addition product has side effects.

Gemcitabine has relatively large toxic and side effects, and the liver specific delivery technology is utilized to enhance the concentration in the liver, which is beneficial to reducing the toxic and side effects.

At present, there is no anti-liver-tumor drug with high activity, strong liver delivery property and low side effects. Therefore, there is an urgent need in the art to develop a highly active anti-tumor drug having stronger liver specificity and low side effects.

SUMMARY

The present disclosure synthesizes anti-cancer gemcitabine cyclic phosphate, and then further modifies an aromatic ring substituent thereof to obtain a class of prodrugs with better liver delivery effect, so that the present disclosure has the advantages of higher curative effect and less toxic and side effect.

A first aspect of the present disclosure provides a compound as represented by following formula I, or an optical isomer, a pharmaceutically acceptable salt, a hydrate or a solvate thereof:

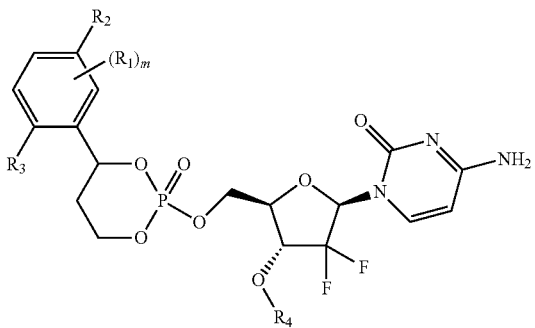

wherein

R1 is each independently selected from the group consisting of halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, substituted or unsubstituted C2-C6 ester group, substituted or unsubstituted C2-C6 alkanoyl, and substituted or unsubstituted C2-C6 alkylamido, wherein the "substituted" means having one or more substituents selected from the group consisting of: halogen, C1-C3 alkyl, C1-C3 haloalkyl, nitro, hydroxy, amino, and cyano;

R2 and R3 are each independently halogen (F or Cl)

R4 is selected from the group consisting of: hydrogen, substituted or unsubstituted C1-C6 alkyl, substituted or unsubstituted C3-C8 cycloalkyl, substituted or unsubstituted C2-C6 ester group, and substituted or unsubstituted C2-C10 alkanoyl, wherein the "substituted" means having one or more substituents selected from the group consisting of: halogen, C1-C3 alkyl, C1-C3 haloalkyl, nitro, hydroxy, amino and cyano; and m is 0, 1, 2 or 3.

In another preferred example, R4 is selected from the group consisting of: hydrogen, substituted or unsubstituted C1-C6 alkyl, substituted or unsubstituted C3-C8 cycloalkyl, substituted or unsubstituted C2-C6 ester group, and substituted or unsubstituted C2-C6 alkanoyl, and wherein the "substituted" means having one or more substituents selected from the group consisting of: halogen, C1-C3 alkyl, C1-C3 haloalkyl, nitro, hydroxyl, amino and cyano.

In another preferred example, the compound is selected from the group consisting of:

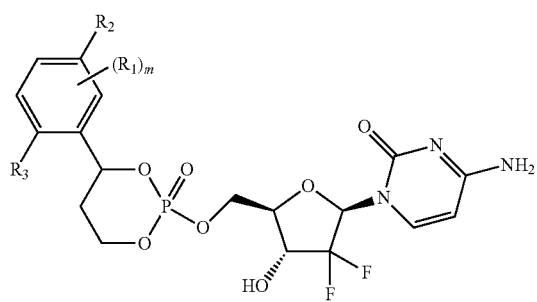

II

R2 and R3 are each independently halogen (F or Cl);

Moreover, in the formula I and the formula II, except existing chirality, various other chiral centers are in R type or S type;

In another preferred example, R2 is Cl, and R3 is F; R2 is Cl, and R3 is Cl; or R2 is F, and R3 is Cl.

In another preferred example, the optical isomer includes tautomers, cis-trans isomers, conformers, meso compounds and optical isomers in enantiomeric or diastereomeric relationship.

In another preferred example, the compound is selected from the group consisting of:

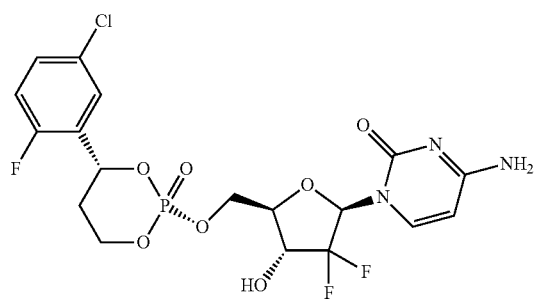

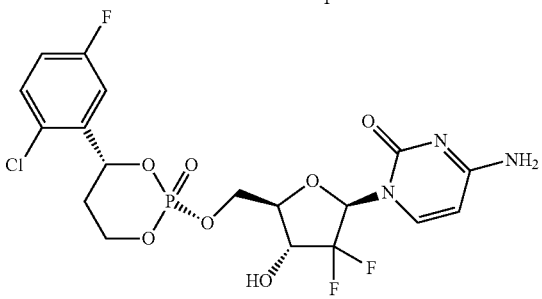

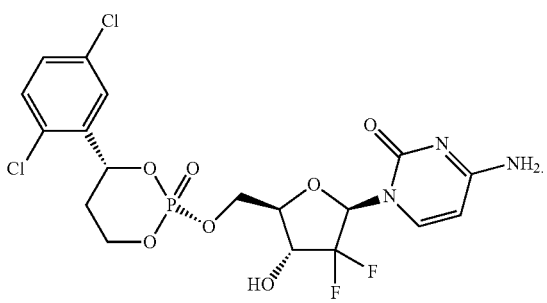

In another preferred example, salts of compounds represented by the formula I and the formula II are pharmaceutically acceptable salts formed by the compounds represented by the formula I and the formula II and an inorganic acid or an organic acid, or the salts of the compounds represented by the formula I and the formula II are pharmaceutically acceptable salts formed by the reaction between the compounds represented by the formula I and the formula II and a base. The compounds represented by the formula I and the formula II or salts thereof are amorphous substances or crystals.

A second aspect of the present disclosure provides a pharmaceutical composition, wherein the pharmaceutical composition includes a therapeutically effective amount of the compound, or an optical isomer, a pharmaceutically acceptable salt, a hydrate or a solvate thereof, as described in the first aspect of the present disclosure; and a pharmaceutically acceptable adjuvant, a diluent or a carrier.

A third aspect of the present disclosure provides use of the compound, or an optical isomer, a pharmaceutically acceptable salt, a hydrate or a solvate thereof, as described in the first aspect of the present disclosure, in a preparation of a pharmaceutical composition for treating and/or preventing acute or chronic diseases associated with hepatocellular carcinoma (HCC).

A fourth aspect of the present disclosure provides a method for preparing the compound of the formula I as described in the first aspect of the present disclosure, wherein the method includes following steps:

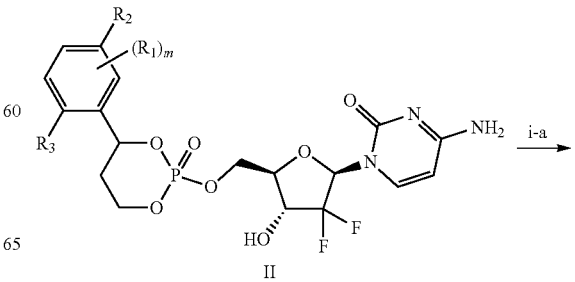

II

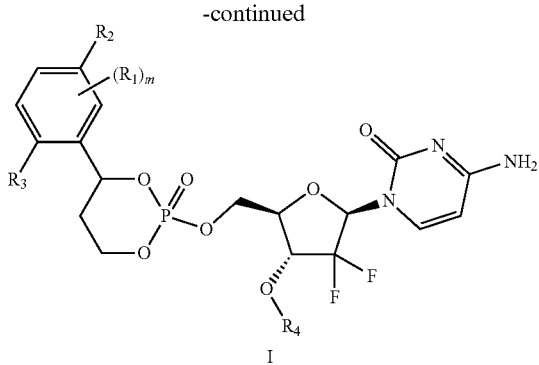

I (i-a) Making a compound of the formula II undergo a reaction with an acid, an acyl chloride, and a haloalkyl in an inert solvent to form a compound of the formula I, wherein in the formulas, each group is as defined above.

In another preferred example, in the step (i-a), the reagent is selected from the group consisting of: dicyclohexylcarbodiimide (DCC), triethylamine, N,N-diisopropylethylamine, or a combination thereof, and is preferably DCC and triethylamine.

In another preferred example, in the step (i-a), the inert solvent is selected from the group consisting of: N,N-dimethylformamide, dichloromethane, tetrahydrofuran, or a combination thereof, and is preferably N,N-dimethylformamide and dichloromethane solvent.

In another preferred example, a reaction temperature in the step (i-a) is 0-100° C. (preferably around 25±5° C.).

In another preferred example, reaction time of deprotection reaction in the step (i-a) is 0.5-24 hours, and preferably 0.5-8 hours.

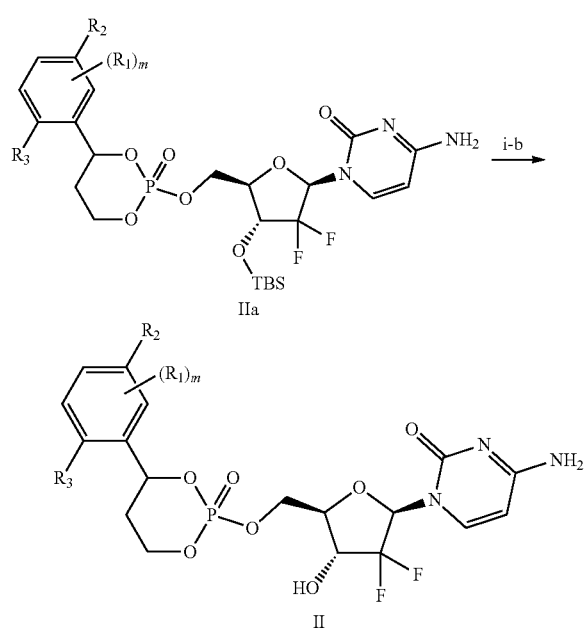

(i-b) Removing TBS from a compound of the formula IIa in an inert solvent to form the compound of the formula II.

In another preferred example, in the step (i-b), a TBS removal reagent is selected from the group consisting of: TBAF, glacial acetic acid, dilute hydrochloric acid, or a combination thereof, and is preferably hydrochloric alcohol solution and TBAF.

In another preferred example, in the step (i-b), the inert solvent is selected from the group consisting of: N,N-dimethylformamide, tetrahydrofuran, or a combination thereof, and is preferably tetrahydrofuran solvent.

In another preferred example, a reaction temperature in the step (i-b) is −50-30° C. (preferably around 25±5° C.).

In another preferred example, reaction time of deprotection reaction in the step (i-b) is 0.5-6 hours, preferably 0.5-3 hours, and more preferably 0.5-2 hours.

In another preferred example, the compound of formula IIa is prepared by a following method:

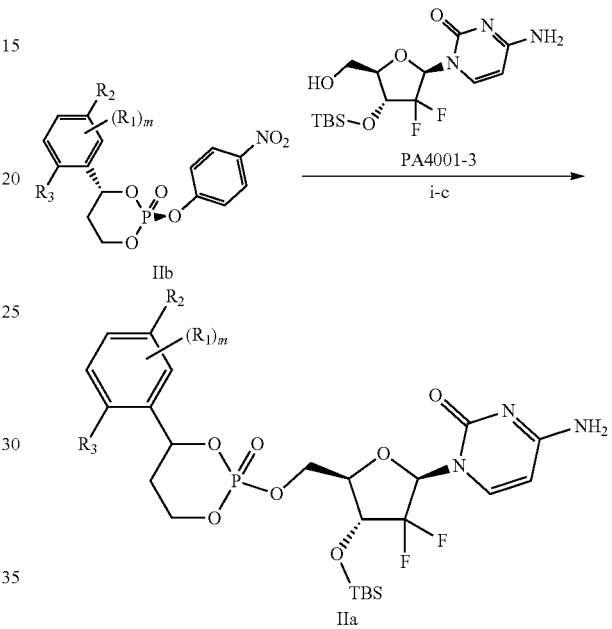

(i-c) Making a compound of the formula IIb undergo substitution reaction with PA4001-3 in an inert solvent to obtain the compound of formula IIa.

In another preferred embodiment, in the step (i-c), the reaction is carried out in the presence of a Grignard reagent; and preferably, the Grignard reagent is selected from the group consisting of: tert-butylmagnesium chloride (t-BuMgCl).

In another preferred example, the substitution reaction in the step (i-c) is carried out at −50-30° C. (preferably around 25±5° C.).

In another preferred example, reaction time of the substitution reaction in the step (i-c) is 1-72 hours, preferably 3-48 hours, and more preferably 6-24 hours.

In another preferred example, the inert solvent in the step (i-c) is selected from the group consisting of: N,N-dimethylformamide, tetrahydrofuran, or a combination thereof, and is preferably tetrahydrofuran solvent.

Notes:

dFdC: gemcitabine, 4-amino-1-(3,3-difluoro-4-hydroxy-5-hydroxymethyltetrahydrofuran-2-yl)-1H-pyrimidin-2-one, CAS: 95058-81-4 dFdCMP: 4-amino-1-(3,3-difluoro-4-hydroxy-5-monophosphate methylenetetrahydrofuran-2-yl)-1H-pyrimidin-2-one It should be understood that within the scope of the present disclosure, various technical features of the present disclosure described above and various technical features specifically described below (e.g., in the examples) may be combined with each other, so as to form new or preferred technical solutions, which are not repeated herein one by one due to space limitation.

DETAILED DESCRIPTION OF EMBODIMENTS

Through long-term and in-depth research, by screening and researching a large number of compounds, the inventors found for the first time that a class of compounds of formula I and formula II having specific structures (wherein site 2 and site 5 of benzene ring moiety are specific halogens) surprisingly had quite excellent activity against liver cancer, significantly improved liver delivery property and significantly reduced toxic and side effects. Based on the above findings, the inventors completed the present disclosure.

Terms

As used herein, the term "C1-C6 alkyl" refers to a straight or branched chain alkyl having 1~6 carbon atoms, for example, methyl, ethyl, propyl, isopropyl, butyl, isobutyl, sec-butyl, tert-butyl, or similar groups.

As used herein, the term "C2-C6 alkanoyl" refers to a substituent shaped like a structure "straight or branched chain alkyl-carbonyl having 1~6 carbon atoms", for example, acetyl, propionyl, butyryl, or similar groups.

As used herein, the term "C1-C6 alkylamino" refers to a substituent shaped like a structure "straight or branched chain alkyl-amino having 1~6 carbon atoms", for example, methylamino, dimethylamino, ethylamino, propylamino, diethylamino, or similar groups.

The term "halogen" refers to F, Cl, Br and I.

In the present disclosure, the terms "containing", "including" or "comprising" mean that various ingredients may be used together in a mixture or composition of the present disclosure. Thus, the terms "consisting essentially of . . ." and "consisting of . . ." are encompassed by the term "containing".

In the present disclosure, the term "pharmaceutically acceptable" ingredient refers to a substance that is suitable for humans and/or animals without undue adverse side effects (such as toxicity, irritation and allergic response), i.e., at a reasonable benefit/risk ratio.

In the present disclosure, the term "effective amount" refers to an amount of a therapeutic agent for treatment, amelioration or prevention of a target disease or condition, or an amount that exhibits a detectable therapeutic or prophylactic effect. A precise effective amount for a certain subject depends upon the body size and health condition of the subject, the nature and extent of the disorder, and a therapeutic agent and/or a combination of therapeutic agents selected for administration. Therefore, it is not useful to specify an accurate effective amount in advance. However, for a given condition, routine experimentation can be used to determine the effective amount, which can be determined by clinicians.

Herein, unless otherwise specified, the term "substituted" means that one or more hydrogen atoms on a group are substituted with a substituent selected from the group consisting of: halogen, C1-C3 alkyl, C1-C3 haloalkyl, nitro, hydroxyl, amino and cyano.

Unless otherwise specified, all compounds appearing in the present disclosure are intended to include all possible optical isomers, such as single chiral compounds, or a mixture (i.e., racemate) of various different chiral compounds. In all compounds of the present disclosure, each chiral carbon atom may optionally be in R configuration or S configuration, or a mixture of R configuration and S configuration.

As used herein, the term "compound of the present disclosure" refers to compounds represented by formula I and formula II. The term also includes various crystalline forms, pharmaceutically acceptable salts, hydrates or solvates of the compounds represented by the formula I and the formula II.

As used herein, the term "pharmaceutically acceptable salt" refers to a salt formed by the compound of the present disclosure and an acid or a base, suitable for acting as a pharmaceutical. The pharmaceutically acceptable salt includes inorganic salts and organic salts. One class of preferred salts are salts that formed by the compounds of the present disclosure and an acid. Acids suitable for forming salts include, but are not limited to: inorganic acids such as hydrochloric acid, hydrobromic acid, hydrofluoric acid, sulfuric acid, nitric acid, and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid, and benzenesulfonic acid; and acidic amino acids such as aspartic acid and glutamic acid.

Some compounds in the present disclosure may be crystallized or recrystallized using water or various organic solvents, in which case various solvates may be formed. Solvates in the present disclosure include stoichiometric solvates such as hydrates, as well as compounds formed when prepared by the low pressure sublimation drying method and containing a variable amount of water.

It should be understood that there may be a variety of thermodynamically stable isomers after the compound of the present disclosure is prepared, such as tautomers, conformers, meso compounds and optical isomers in enantiomeric or diastereomeric relationship, and the above variations will be apparent to those skilled in the art after reading the present disclosure.

Compound of Formula I and Preparation Thereof

In order to provide a high-efficiency and low-toxicity liver delivery prodrug capable of enabling anti-cancer nucleotide drugs to be released intensively in hepatocytes through a liver delivery mechanism, the inventors prepared a compound of formula I:

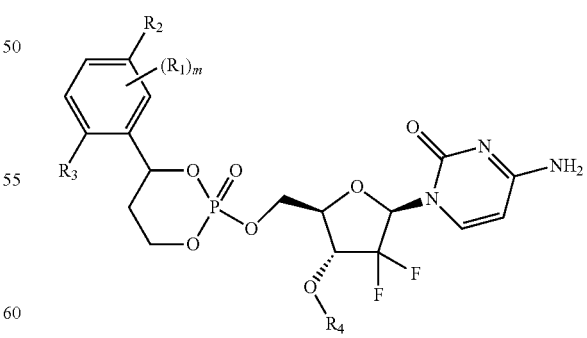

wherein

R1 is each independently selected from the group consisting of halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, substituted or unsubstituted C1-C6 ester group, substituted or unsubstituted C2-C6 alkanoyl, and substituted or unsubstituted C2-C6 alkylamido, wherein the "substituted" means having one or more substituents selected from the group consisting of: halogen, C1-C3 alkyl, C1-C3 haloalkyl, nitro, hydroxy, amino, and cyano;

R2 and R3 are each independently halogen (F or Cl);

R4 is independently selected from the group consisting of: hydrogen, substituted or unsubstituted C1-C6 alkyl, substituted or unsubstituted C3-C8 cycloalkyl, substituted or unsubstituted C1-C6 ester group, and substituted or unsubstituted C2-C6 alkanoyl, wherein the "substituted" means having one or more substituents selected from the group consisting of: halogen, C1-C3 alkyl, C1-C3 haloalkyl, nitro, hydroxyl, amino and cyano; and m is 0, 1, 2, or 3.

Moreover, in the formula I, except existing chirality, various other chiral centers are in R type or S type;

The compound may be a racemate, or an optical isomer, both of which have certain anti-cancer activity. Preferably, the compound of the formula I has a structure selected from the group consisting of:

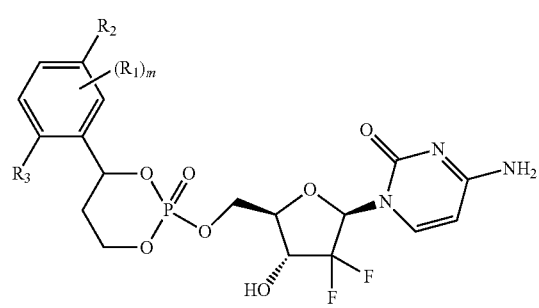

II

In another preferred example, the P2 and aromatic group at site 4 of the phosphate ring structure are cis with each other, and the P2 is in R configuration, and the C4 is in S type.

In another preferred example, R2 is Cl, and R3 is F; R2 is Cl, and R3 is Cl; or R2 is F, and R3 is Cl.

In another preferred example, the optical isomer includes tautomers, cis-trans isomers, conformers, meso compounds and optical isomers in enantiomeric or diastereomeric relationship.

In another preferred example, the compound is selected from the following group:

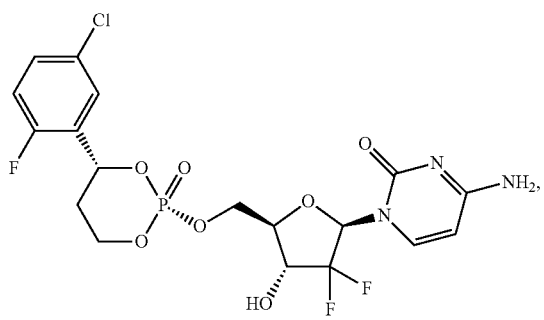

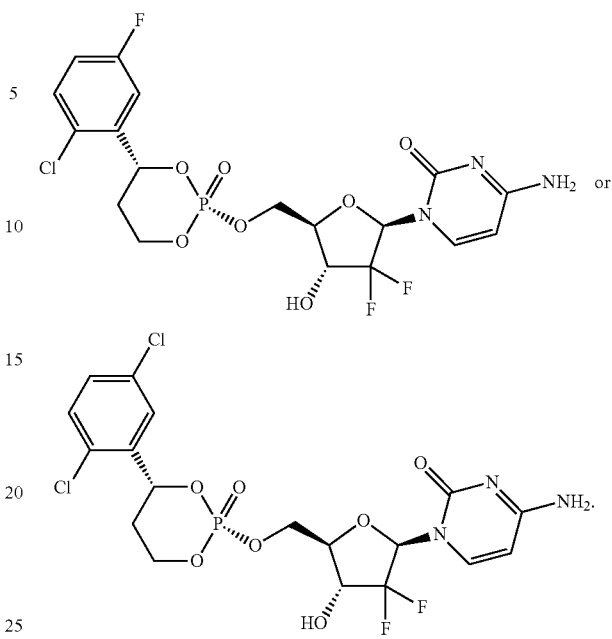

A Method for Preparing the Compound of the General Formula I is as Follows:

In a tetrahydrofuran solution, a compound PA4001-3 is added, then t-butylmagnesium chloride is added dropwise at 0° C., followed by reaction for 30 minutes, then an IIb compound is added all at once, followed by reaction overnight, quenching, and purification by silica gel column chromatography to obtain an intermediate a. IIa is added to a hydrochloric alcohol solution, and a protecting group TBS is removed to obtain a compound of general formula II. II reacts with acid, acyl chloride, haloalkyl to obtain the compound of the general formula I.

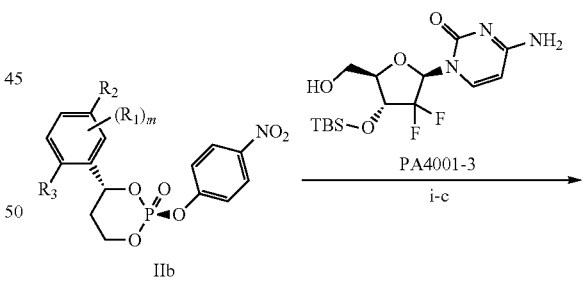

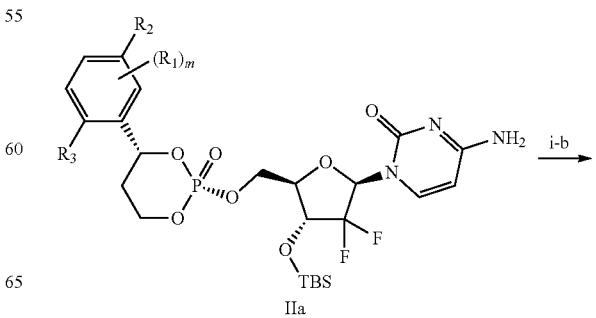

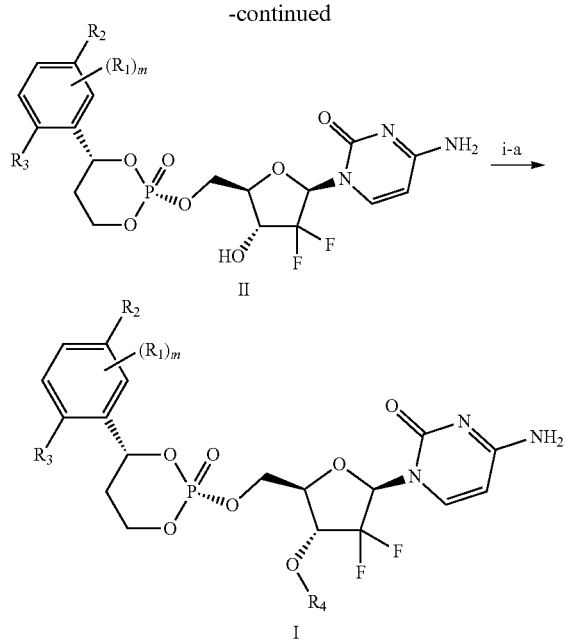

In the above, each reactant may be obtained by commercially available routes, and may also be prepared by conventional methods in the art using commercially available raw materials.

Pharmaceutical Composition and Method of Administration

As the compounds of the present disclosure have excellent inhibitory activity on liver cancer, the compound of the present disclosure and various crystal forms thereof, pharmaceutically acceptable inorganic or organic salts, hydrates or solvates, and pharmaceutical compositions containing the compound of the present disclosure acting as a main active ingredient may be used for treatment, prevention and alleviation of cancers, especially liver cancer and related symptoms thereof.

The pharmaceutical composition of the present disclosure contains a safe and effective amount of the compound of the present disclosure, or a pharmacologically acceptable salt thereof and a pharmacologically acceptable excipient or carrier. In the above, "safe and effective amount" means that the amount of the compound is sufficient to significantly improve the condition without causing severe side effects. Generally, the pharmaceutical composition contains 0.1-1000 mg of the compound of the present disclosure/dose, more preferably 0.5~500 mg of the compound of the present disclosure/dose. Preferably, "one dose" is one capsule or tablet.

"Pharmaceutically acceptable carrier" refers to one or more compatible solids or liquid fillers or gel substances that are suitable for human use and must be of sufficient purity and sufficiently low toxicity. "Compatibility" herein means that various components in the composition can be intermingled with the compound of the present disclosure and with each other, without significantly reducing the efficacy of the compound. Examples of pharmaceutically acceptable carrier moieties include celluloses and derivatives thereof (such as sodium carboxymethylcellulose, sodium ethylcellulose, and cellulose acetate), gelatin, talc, solid lubricants (such as stearic acid and magnesium stearate), calcium sulfate, vegetable oils (such as soy oil, sesame oil, peanut oil, and olive oil), polyols (such as propylene glycol, glycerol, mannitol, and sorbitol), emulsifiers (such as Tween®), wetting agents (such as lauryl sodium sulfate), colorants, flavoring agents, stabilizers, antioxidants, preservatives, pyrogen-free water and so on.

A mode of administration of the compound or pharmaceutical composition of the present disclosure is not particularly limited, and representative modes of administration include (but are not limited to) oral, rectal, parenteral (intravenous, intramuscular or subcutaneous), and topical administration. A particularly preferred mode of administration is oral administration.

Solid dosage forms used for oral administration include capsule, tablet, pill, powder and granule. In these solid dosage forms, the active compound is mixed with at least one conventional inert excipient (or carrier), such as sodium citrate or dicalcium phosphate, or mixed with following ingredients: (a) a filler or a compatibilizer, for example, starch, lactose, sucrose, glucose, mannitol and silicic acid; (b) a binder, for example, hydroxymethyl cellulose, alginate, gelatin, polyvinylpyrrolidone, sucrose and Arabic gum; (c) a humectant, for example, glycerol; (d) a disintegrant, for example, agar, calcium carbonate, potato starch or tapioca starch, alginic acid, certain complex silicates, and sodium carbonate; (e) a slow solvent, for example, paraffin; (f) an absorption accelerator, for example, quaternary amine compounds; (g) a wetting agent, for example, cetyl alcohol and glyceryl monostearate; (h) an adsorbent, for example, kaolin; and (i) a lubricant, for example, talc, calcium stearate, magnesium stearate, solid polyethylene glycol, lauryl sodium sulfate, or mixtures thereof. In the capsule, tablet and pill, the dosage forms may also contain a buffer.

Solid dosage forms such as tablet, sugar pill, capsule, pill and granule can be prepared using coatings and shell materials such as enteric coatings and other materials commonly known in the art. They may contain an opacifying agent, and the active compound or compound in such composition may be released in a certain part within the digestive tract in a delayed manner. Examples of embedding components that may be employed are polymeric substances and waxy substances. If necessary, the active compound may also form a microcapsule form with one or more of the above excipients.

Liquid dosage forms used for oral administration include pharmaceutically acceptable emulsion, solution, suspension, syrup or tincture. In addition to the active compound, the liquid dosage form may contain an inert diluent conventionally used in the art, such as water or other solvents, a solubilizer and an emulsifier, for example, ethanol, isopropanol, ethyl carbonate, ethyl acetate, propylene glycol, 1,3-butanediol, dimethylformamide and oils, in particular cottonseed oil, peanut oil, maize germ oil, olive oil, castor oil and sesame oil, or a mixture of these substances.

In addition to these inert diluents, the composition may also contain an adjuvant such as wetting agent, emulsifier, suspending agent, sweetener, corrigent and fragrance.

In addition to the active compounds, the suspension may contain a suspending agent, for example, ethoxylated isooctadecanol, polyoxyethylene sorbitol and sorbitan ester, microcrystalline cellulose, aluminum methoxide and agar, or a mixture of these substances.

A composition used for parenteral injection may contain a physiologically acceptable sterile aqueous or anhydrous solution, dispersion liquid, suspension or emulsion, and sterile powder for redissolution into sterile injectable solution or dispersion liquid. Suitable aqueous and non-aqueous carrier, diluent, solvent or excipient includes water, ethanol, polyol and suitable mixtures thereof.

Dosage forms of the compound of the present disclosure used for topical administration include ointment, powder, patch, spraying agent and inhalant. The active ingredients are mixed together, under sterile condition, with a physiologically acceptable carrier and any preservative, buffer, or propellant that may be needed as necessary.

The compound of the present disclosure may be administered alone or in combination with other pharmaceutically acceptable compounds.

When the pharmaceutical composition is used, a safe and effective amount of the compound of the present disclosure is applied to a mammal (such as a human) in need of treatment, wherein the dose when administered is a pharmaceutically recognized effective dosage of administration, and for a person having a body weight of 60 kg, the daily dosage of administration is usually 0.2~1000 mg, preferably 0.5~500 mg. Of course, factors such as the route of administration and the health condition of the patient should also be taken into account for the specific dosage, which is within the skill range of skilled physicians.

Main Advantages of the Present Disclosure Include:

(1) With high liver delivery property, the compound can only be specifically catalyzed by CYP3A in the cytochrome P450 isoenzyme family in hepatocytes to generate active molecules, and the active molecules carry high negative charges and are not easy to be discharged out of the liver, therefore, the concentration in the liver is higher, and thus the liver delivery effect is achieved.

(2) The activity is high, and due to the liver delivery property, more drugs exist in the liver, and the anti-cancer activity can also be greatly improved.

(3) The toxic and side effects are low: for an equivalent dosage of prodrug, a quite small amount is metabolized into active molecules outside the liver, therefore, the toxicity to major organs such as kidney and bone marrow is greatly reduced.

The present disclosure is further illustrated below in combination with specific examples. It should be understood that these examples are merely used to illustrate the present disclosure rather than limiting the scope of the present disclosure. For experimental method whose specific conditions are not specified in the following examples, they are generally carried out under conventional conditions or conditions recommended by manufacturers. Unless otherwise specified, percentages and parts are calculated by weight.

Example 1 PA4001 (Comparative Example)

Synthesis Route:

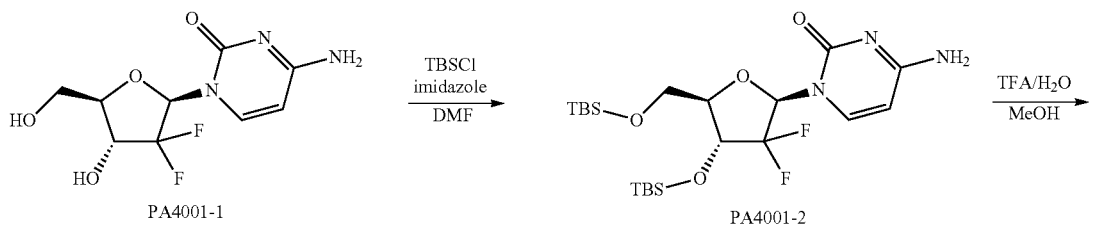

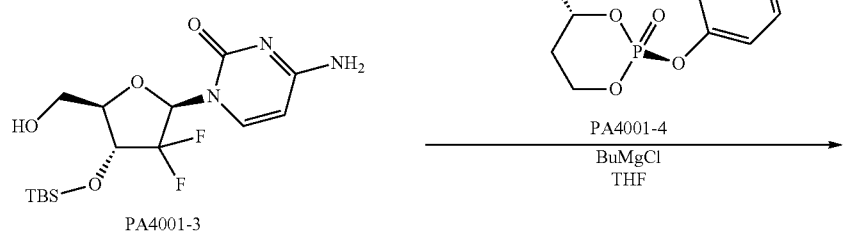

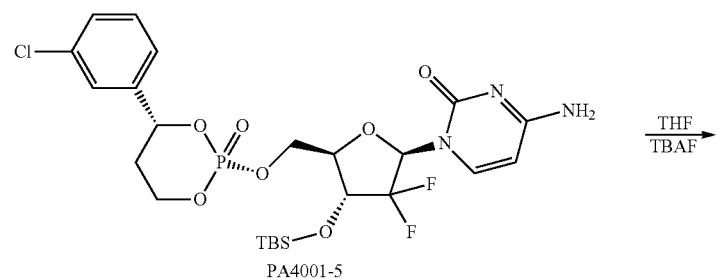

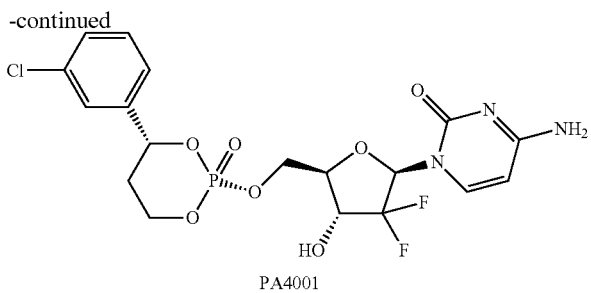

PA4001

Experimental Section:

Step 1) Synthesis of Compound PA4001-2:

dissolving a compound PA4001-1 (5.0 g, 19 mmol) and imidazole (14.3 g, 114 mmol) in DMF (50 mL), adding tert-butyldimethylsilyl chloride (TBSCl, 14.3 g, 95 mmol) slowly in an ice bath, under nitrogen protection, carrying out reaction at room temperature while stirring overnight, after the reaction was ended, adding the resultant slowly to water (400 mL), stirring the mixture for 15 minutes, followed by extraction with ethyl acetate (3×200 mL), drying over anhydrous sodium sulfate, followed by filtration, spin-drying, and separation and purification by silica gel chromatographic column (eluent: MeOH:DCM (V:V)=1:30) to obtain PA4001-2 (9.3 g), with yield of 99%.

Step 2) Synthesis of Compound PA4001-3:

dissolving the compound PA4001-2 (9.3 g, 19 mmol) in methanol (95 mL), adding 40% aqueous trifluoroacetic acid solution (50 ml) in an ice bath, stirring the mixture at room temperature for 3 hours, quickly neutralizing the resultant with a saturated NaHCO3 solution, removing methanol by rotary evaporation, adding water (200 mL), followed by extraction with ethyl acetate (3×150 mL), washing with saturated brine, drying over anhydrous sodium sulfate, followed by filtration, spin-drying, and separation and purification by silica gel chromatographic column (eluent: MeOH:DCM (V:V)=1:20) to obtain a white solid compound PA4001-3 (6.0 g), with yield of 84%.

Step 3) Synthesis of Compound PA4001-5:

dissolving the compound PA4001-3 (377 mg, 1 mmol) in anhydrous tetrahydrofuran, slowly adding 1 M tert-butyl-magnesium chloride solution (3.0 mL, 3.0 mmol) dropwise in an ice bath, stirring the mixture for 2 hours, adding PA4001-4 (442 mg, 1.2 mmol), stirring the mixture at room temperature overnight, adding saturated ammonium chloride (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (DCM:MeOH (V:V)=20:1) to obtain PA4001-5 (270 mg), with yield of 44%.

Step 4) Synthesis of Compound PA4001:

adding the compound PA4001-5 (270 mg, 0.44 mmol) to THF (8 mL), slowly adding 1 mol/L TBAF solution (1 mL) dropwise in an ice bath, stirring the mixture at room temperature for 2 hours, after the reaction was ended, adding 50 mL of water, followed by extraction with ethyl acetate (4×40 mL), washing with saturated brine, drying over anhydrous sodium sulfate, followed by filtration, spin-drying, and separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4001 (33 mg), with yield of 15%.

Example 2 PA4002

Synthesis Route:

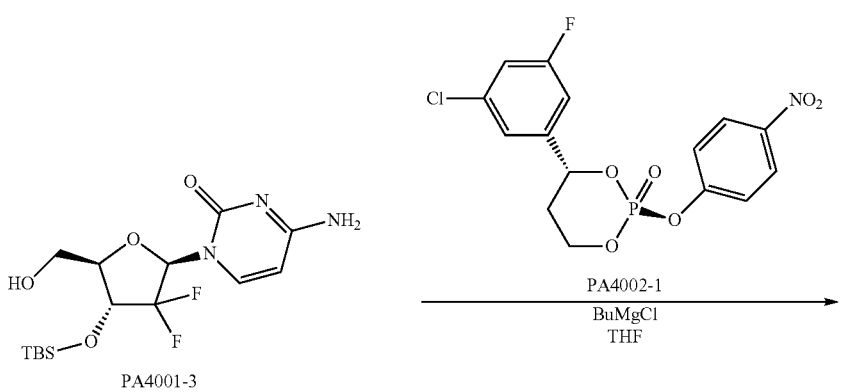

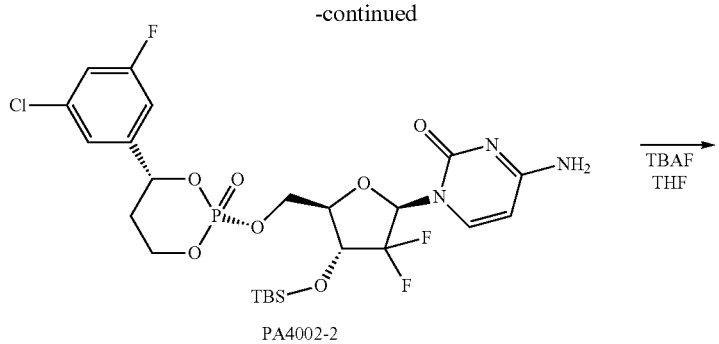

PA4002-2

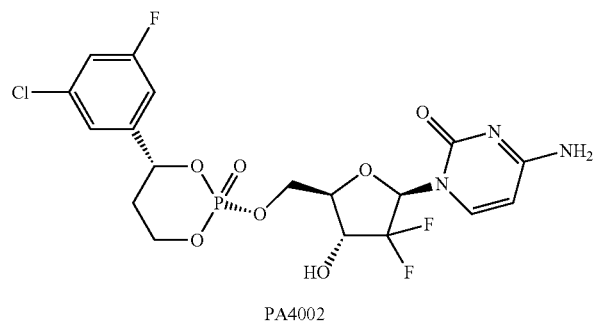

PA4002

Step 1) Synthesis of Compound PA4002-2:

dissolving a compound PA4001-3 (377 mg, 1 mmol) in anhydrous tetrahydrofuran, slowly adding 1 M tert-butylmagnesium chloride solution (3.0 mL, 3.0 mmol) dropwise in an ice bath, stirring the mixture for 2 hours, adding PA4002-1 (464 mg, 1.2 mmol), stirring the mixture at room temperature overnight, after the reaction was ended, adding saturated ammonium chloride (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (DCM:MeOH (V:V)=20:1) to obtain PA4002-2 (90 mg), with yield of 14.3%.

Step 2) Synthesis of Target Compound PA4002 adding the compound PA4002-2 (90 mg, 0.143 mmol) to THF (5 mL), slowly adding 1 mol/L TBAF solution (0.35 mL) dropwise in an ice bath, stirring the mixture at room temperature for 2 h, after the reaction was ended, adding 100 mL of water, followed by extraction with ethyl acetate (3×20 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4002 (14.5 mg), with yield of 19.7%.

Example 3 PA4003

Synthesis Route:

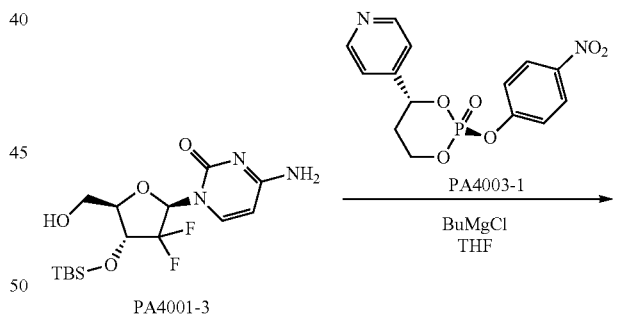

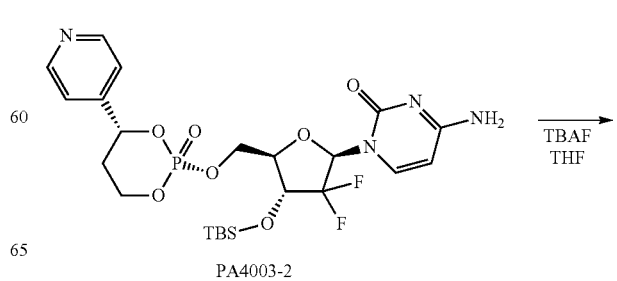

PA4003-2

-continued

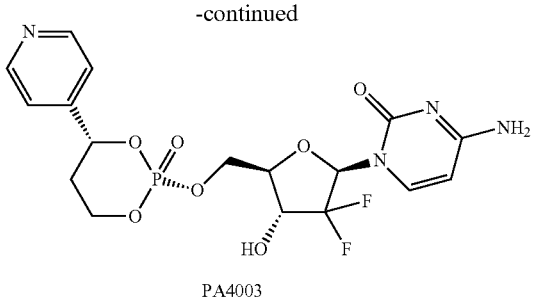

PA4003

Experimental Section:
Step 1) Synthesis of Compound PA4003-2:
dissolving a compound PA4001-3 (377 mg, 1 mmol) in anhydrous tetrahydrofuran, slowly adding 1 M tert-butylmagnesium chloride solution (3.0 mL, 3.0 mmol) dropwise in an ice bath, stirring the mixture for 2 hours, adding PA4003-1 (464 mg, 1.2 mmol), stirring the mixture at room temperature overnight, adding saturated ammonium chloride (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (eluent: DCM:MeOH (V:V)=20:1) to obtain PA4003-2 (250 mg), with yield of 43%.

Step 2) Synthesis of Target Compound PA4003:
adding the compound PA4003-2 (100 mg, 0.174 mmol) to THF (5 mL), slowly adding 1 mol/L TBAF solution (0.42 mL) dropwise in an ice bath, stirring the mixture at room temperature for 2 h, after the reaction was ended, adding 120 mL of water, followed by extraction with ethyl acetate (3×30 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4003 (8 mg), with yield of 10%.

Example 4 PA4004

Synthesis Route:

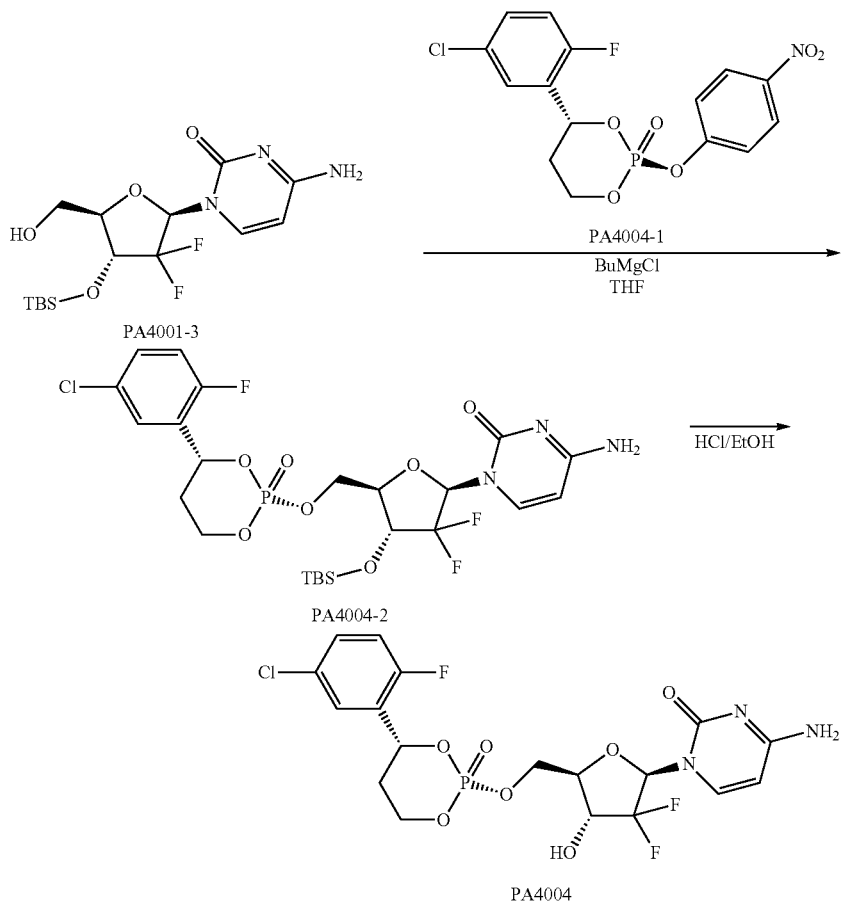

Experimental Section:
Step 1) Synthesis of Compound PA4004-2:
dissolving a compound PA4001-3 (2.0 g, 5.3 mmol) in anhydrous tetrahydrofuran, slowly adding 1 M tert-butylmagnesium chloride solution (18.6 mL, 18.55 mmol) dropwise in an ice bath, stirring the mixture for 2 hours, adding PA4004-1 (3.07 g, 7.95 mmol), stirring the mixture at room temperature overnight, after the reaction was ended, adding saturated ammonium chloride (100 mL) to quench the reaction, followed by extraction with ethyl acetate (3×80 mL), washing with saturated brine, drying over anhydrous sodium sulfate, followed by filtration, spin-drying, and separation and purification by silica gel chromatographic column (eluent: DCM:MeOH (V:V)=20:1) to obtain PA4004-2 (1.6 g), with yield of 48%.

Step 2) Synthesis of Target Compound PA4004:

adding the compound PA4004-2 (1.6 g, 2.56 mmol) to 25% hydrochloric alcohol solution (12 ml), and stirring the mixture at room temperature for 4 h, after the reaction was ended, neutralizing the resultant to make a pH value be neutral with a saturated NaHCO3 solution, after removing ethanol by rotary evaporation, adding water 100 ml, followed by extraction with ethyl acetate (4×80 mL), washing with saturated brine, drying over anhydrous sodium sulfate, followed by filtration, spin-drying, and purification by Combiflash chromatography column to obtain a pale white solid PA4004 (1.05 g), with yield of 80%.

Example 5 PA4006

Synthesis Route:

Experimental Section:

Step 1) Synthesis of Compound PA4006-2 dissolving a compound PA4001-3 (300 mg, 0.8 mmol) in anhydrous tetrahydrofuran, slowly adding 1 M tert-butyl-magnesium chloride solution (2.8 mL, 2.8 mmol) dropwise in an ice bath, stirring the mixture for 2 hours, adding PA4006-1 (482 mg, 1.2 mmol), stirring the mixture at room temperature overnight, after the reaction was ended, adding a saturated ammonium chloride solution (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (DCM:MeOH (V:V)=20:1) to obtain PA4006-2 (180 mg), with yield of 35%.

Step 2) Synthesis of Target Compound PA4006 adding the compound PA4006-2 (180 mg, 0.28 mmol) to MeOH (3 mL), slowly adding a TFA solution (1 mL) dropwise in an ice bath, stirring the mixture at room temperature for 16 h, after the reaction was ended, adding 100 mL of water, followed by extraction with ethyl acetate (3×20 mL), washing with saturated brine, drying over anhydrous sodium sulfate, followed by filtration, spin-drying, separa-

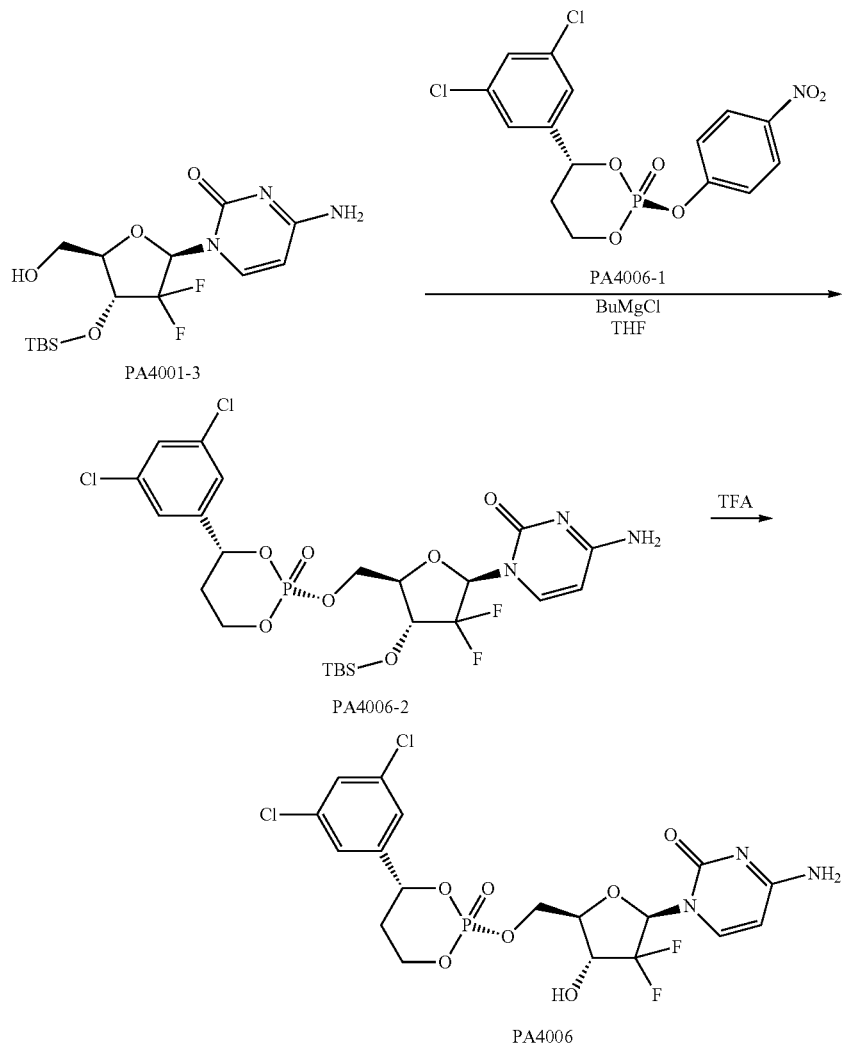

tion and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4006 (40 mg), with yield of 27%.

Example 6 PA4008

Synthesis Route:

saturated ammonium chloride (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (DCM:MeOH (V:V)=20:1) to obtain PA4008-2 (190 mg), with yield of 38%.

Step 2) Synthesis of Target Compound PA4008:
adding the compound PA4008-2 (190 mg, 0.3 mmol) to MeOH (3 mL), slowly adding a TFA solution (1 mL) dropwise in an ice bath, stirring the mixture at room tem-

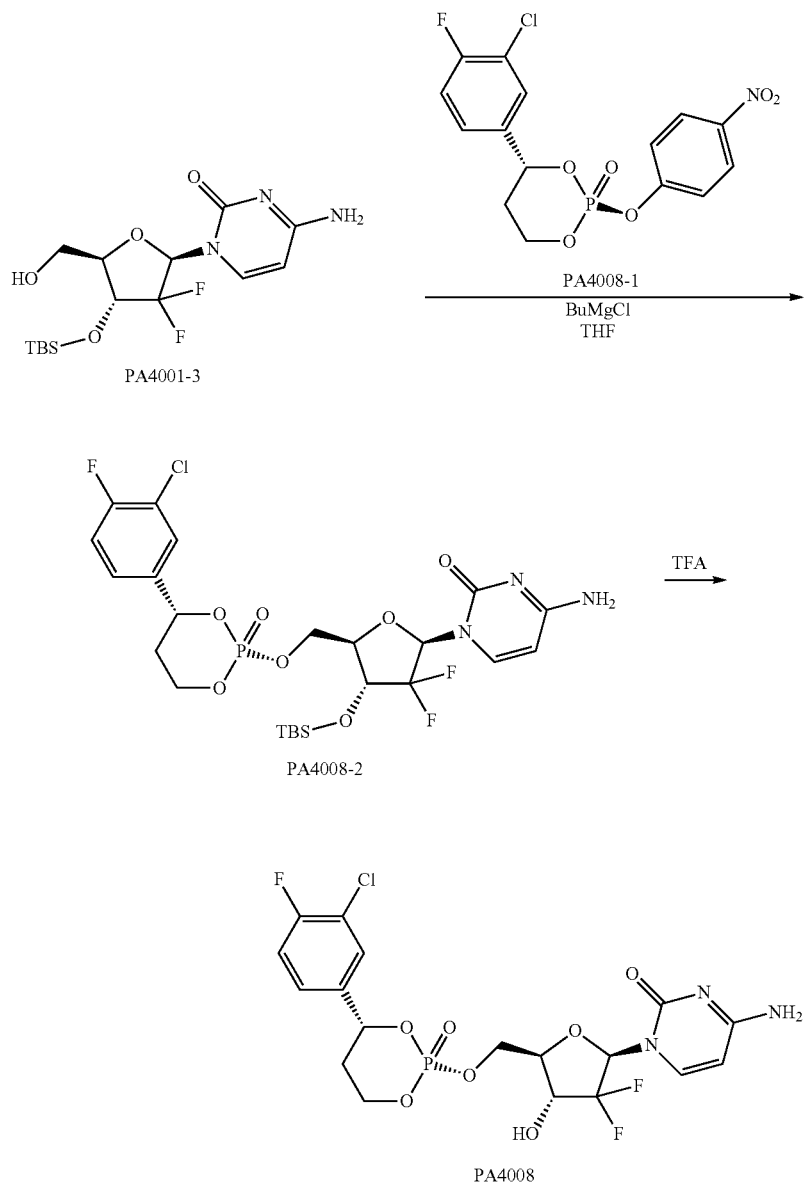

Experimental Section:
Step 1) Synthesis of Compound PA4008-2
dissolving a compound PA4001-3 (300 mg, 0.8 mmol) in anhydrous tetrahydrofuran, slowly adding 1 M tert-butylmagnesium chloride solution (2.8 mL, 2.8 mmol) dropwise in an ice bath, stirring the mixture for 2 hours, adding PA4008-1 (464 mg, 1.2 mmol), stirring the mixture at room temperature overnight, after the reaction was ended, adding perature for 16 h, after the reaction was ended, adding water 100 ml, followed by extraction with ethyl acetate (3×20 mL), washing with saturated brine, drying over anhydrous sodium sulfate, followed by filtration, spin-drying, and purification by Combiflash chromatography column, and lyophylization to obtain a pale white solid PA4008 (123 mg), with yield of 79%.

Example 7 PA4009

Synthesis Route:

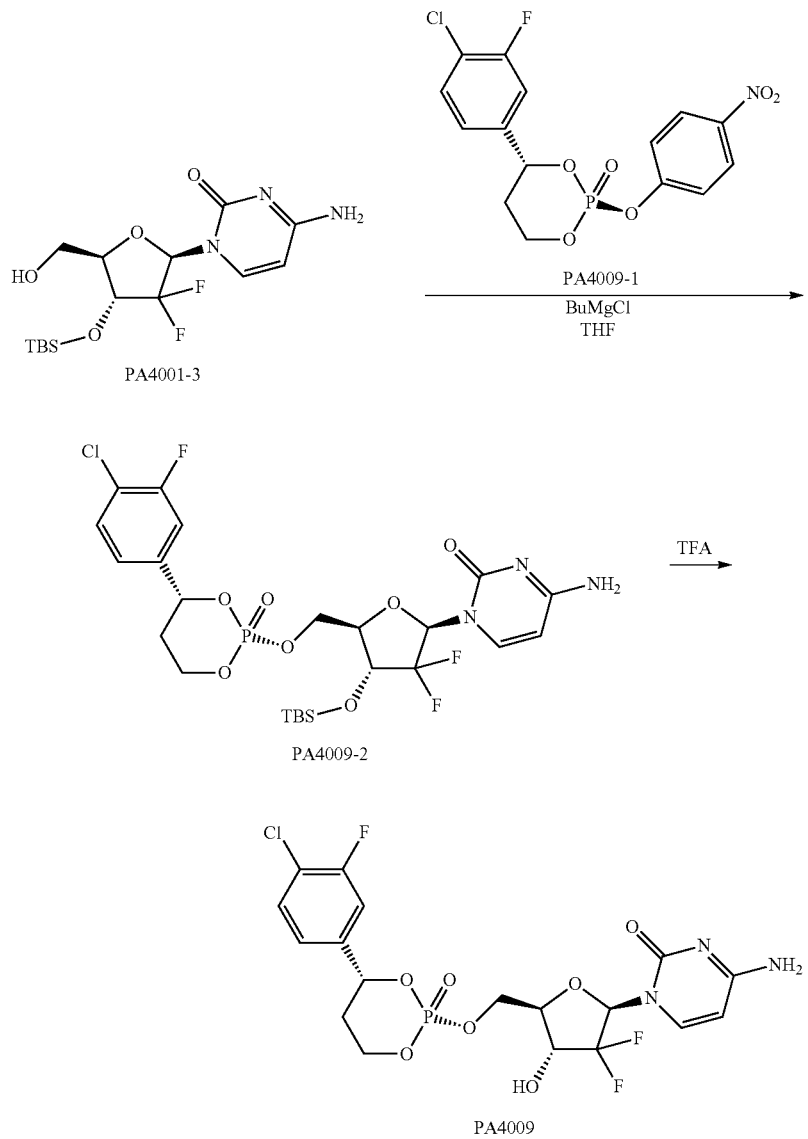

Experimental Section:

Step 1) Synthesis of Compound PA4009-2 dissolving a compound PA4001-3 (300 mg, 0.8 mmol) in anhydrous tetrahydrofuran, slowly adding 1 M tert-butyl-magnesium chloride solution (2.8 mL, 2.8 mmol) dropwise in an ice bath, stirring the mixture for 2 hours, adding PA4009-1 (464 mg, 1.2 mmol), stirring the mixture at room temperature overnight, after the reaction was ended, adding saturated ammonium chloride (20 mL) to quench the reaction, followed by extraction with ethyl acetate (3×30 mL), washing with saturated brine, drying over anhydrous sodium sulfate, followed by filtration, spin-drying, and separation and purification by silica gel chromatographic column (eluent: DCM:MeOH (V:V)=20:1) to obtain PA4009-2 (230 mg), with yield of 46%.

Step 2) Synthesis of Target Compound PA4009 adding the compound PA4009-2 (230 mg, 0.37 mmol) to MeOH (3 mL), slowly adding a TFA solution (1 mL) dropwise in an ice bath, stirring the mixture at room temperature for 16 h, after the reaction was ended, adding 100 mL of water, followed by extraction with ethyl acetate (3×20 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4009 (45 mg), with yield of 24%.

Example 8 PA4010

Synthesis Route:

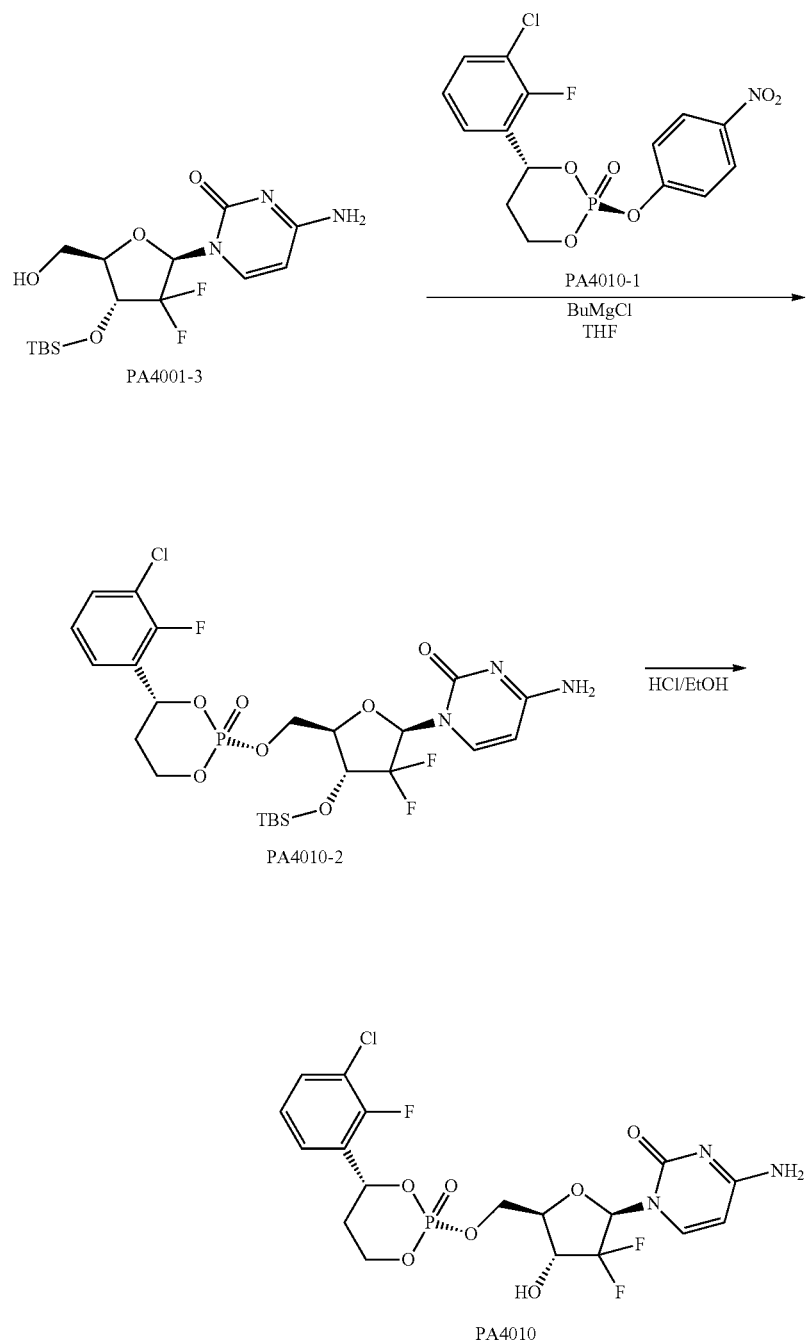

Experimental Section:

Step 1) Synthesis of Compound PA4010-2 dissolving a compound PA4001-3 (320 mg, 0.85 mmol) in anhydrous tetrahydrofuran, slowly adding 1 M tert-butylmagnesium chloride solution (3 mL, 3 mmol) dropwise in an ice bath, stirring the mixture for 2 hours, adding PA4010-1 (390 mg, 1.0 mmol), stirring the mixture at room temperature overnight, after the reaction was ended, adding saturated ammonium chloride (100 mL) to quench the reaction, by extraction with ethyl acetate (4×40 mL), washing with saturated brine, drying over anhydrous sodium sulfate, followed by filtration, spin-drying, and purification by Combiflash chromatography column to obtain a pale white solid PA4010 (30 mg), with yield of 20%.

Example 9 PA4011

Synthesis Route:

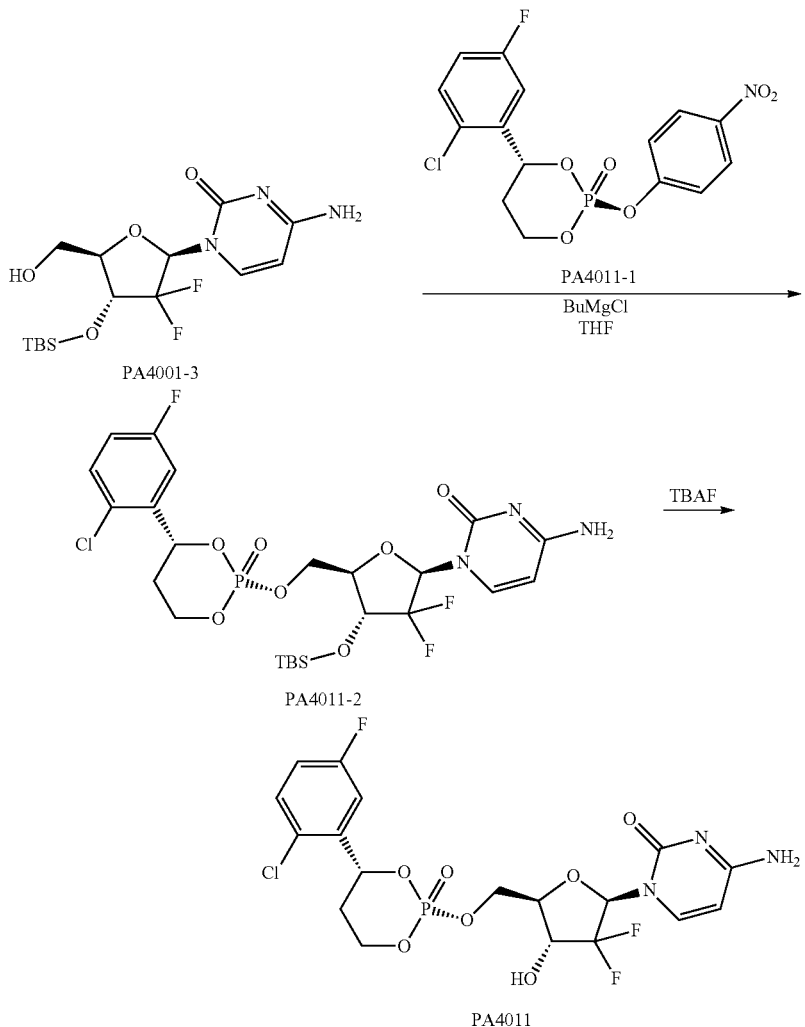

followed by extraction with ethyl acetate (3×50 mL), washing with saturated brine, drying over anhydrous sodium sulfate, followed by filtration, spin-drying, and separation and purification by silica gel chromatographic column (eluent: DCM:MeOH (V:V)=20:1) to obtain PA4010-2 (194 mg), with yield of 36.6%.

Step 2) Synthesis of Target Compound PA4010:

adding the compound PA4010-2 (194 mg, 0.3 mmol) to 25% hydrochloric alcohol solution (4 ml), and stirring the mixture at room temperature for 4 h, after the reaction was ended, neutralizing the resultant to make a pH value be neutral with saturated NaHCO3 solution, after removing ethanol by rotary evaporation, adding water 20 ml, followed Experimental Section:

Step 1) Synthesis of Compound PA4011-2 dissolving a compound PA4001-3 (300 mg, 0.80 mmol) in anhydrous tetrahydrofuran, slowly adding 1 M tert-butylmagnesium chloride solution (2.8 mL, 2.8 mmol) dropwise in an ice bath, stirring the mixture for 2 hours, adding PA4011-1 (464 mg, 1.2 mmol), stirring the mixture at room temperature overnight, after the reaction was ended, adding saturated ammonium chloride (20 mL) to quench the reaction, followed by extraction with ethyl acetate (3×100 mL), washing with saturated brine, drying over anhydrous sodium sulfate, followed by filtration, spin-drying, and separation and purification by silica gel chromatographic column (DCM:MeOH (V:V)=20:1) to obtain PA4011-2 (200 mg), with yield of 40%.

Step 2) Synthesis of Target Compound PA4011 adding the compound PA4011-2 (200 mg, 0.33 mmol) to THF (5 mL), slowly adding 1 mol/L TBAF solution (0.48 mL) dropwise in an ice bath, stirring the mixture at room temperature for 2 h, after the reaction was ended, adding 100 mL of water, followed by extraction with ethyl acetate (3×20 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4011 (95 mg), with yield of 58%.

Example 10 PA4012

Synthesis Route:

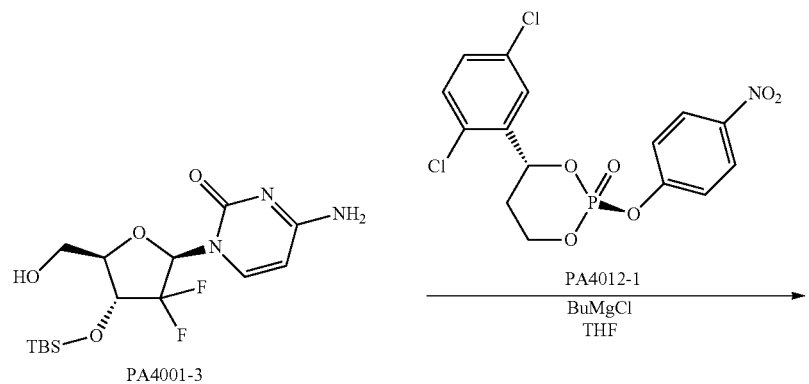

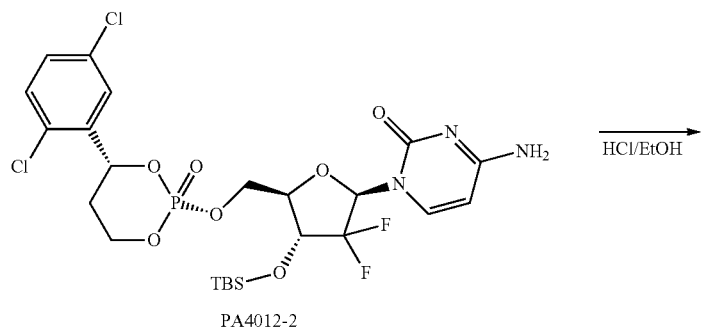

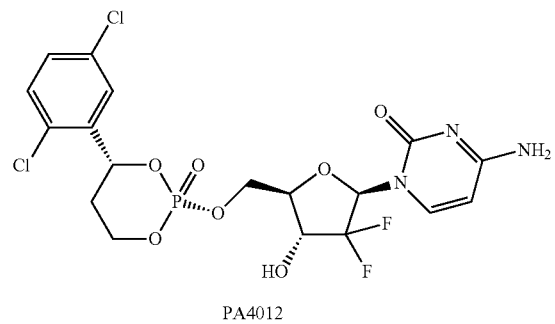

Experimental Section:

Step 1) Synthesis of Compound PA4012-2 dissolving a compound PA4001-3 (300 mg, 0.77 mmol) in tetrahydrofuran (5 mL), slowly adding 1 M tert-butylmagnesium chloride solution (2.7 mL, 2.7 mmol, 3.5 eq) dropwise in an ice bath, after completing the dropwise addition, stirring the reaction solution at room temperature for 2 hours and then cooling the reaction solution to 0° C., adding PA4012-1 (380 mg, 0.92 mmol), then stirring the reaction solution at room temperature overnight, quenching the reaction with a saturated aqueous ammonium chloride solution (30 mL), followed by extraction with ethyl acetate (3×100 mL), drying over anhydrous Na2SO4, followed by filtration, spin-drying, and separation and purification by silica gel chromatographic column (eluent: DCM:MeOH (V:V)=20:1) to obtain a white solid PA4012-2 (280 mg), with yield of 54%.

Step 2) Synthesis of Target Compound PA4012 dissolving the compound PA4012-2 (250 mg, 0.47 mmol) in 3.6% hydrochloric alcohol solution (10 ml), and carrying out reaction while stirring at room temperature for 2 hours, after the reaction was ended, neutralizing the resultant to make a pH value be about 7.5 with a saturated NaHCO3 solution, after removing ethanol by rotary evaporation, extracting the resultant with ethyl acetate (3×60 mL), washing an organic phase with saturated brine, drying over anhydrous sodium sulfate, followed by filtration, spin-drying, separation and purification by silica gel chromatographic column (eluent: DCM:MeOH(V:V)=20:1) to obtain a crude product, and purifying the crude product by Combiflash chromatography column to obtain a pale white solid PA4012 (25 mg), with yield of 11%.

Example 11 PA4013

Synthesis Route:

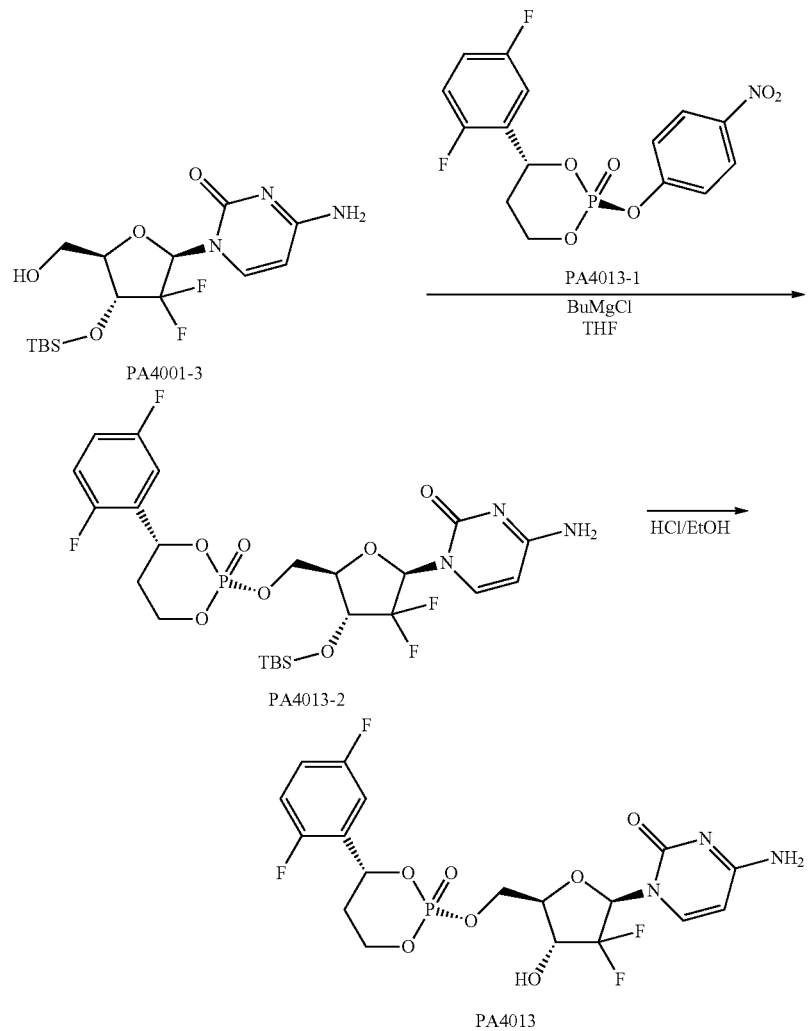

Experimental Section:

Step 1) Synthesis of Compound PA4013-2 dissolving a compound PA4001-3 (377 mg, 1.0 mmol) in tetrahydrofuran (40 mL), slowly adding 1 M tert-butylmagnesium chloride solution (3.5 mL, 3.5 mmol) dropwise in an ice bath, after completing the dropwise addition, stirring the reaction solution at room temperature for 1 hour and then cooling the reaction solution to 0° C., adding PA4013-1 (371 mg, 1.0 mmol), then stirring the reaction solution at room temperature overnight, quenching the reaction with saturated aqueous ammonium chloride solution (30 mL), followed by extraction with ethyl acetate (3×50 mL), drying over anhydrous Na2SO4, followed by filtration, spin-drying, and separation and purification by silica gel chromatographic column (eluent: DCM:MeOH (V:V)=20:1) to obtain a white solid PA4013-2 (218 mg), with yield of 35%.

Step 2) Synthesis of Target Compound PA4013 dissolving the compound PA4013-2 (218 mg, 0.35 mmol) in 3.6% hydrochloric alcohol solution (10 ml), and carrying out reaction while stirring at room temperature for 2 hours, after the reaction was ended, neutralizing the resultant to make a pH value be neutral with a saturated NaHCO3 solution, after removing ethanol by rotary evaporation, extracting the resultant with ethyl acetate (2×70 mL), washing an organic phase with saturated brine, drying over anhydrous sodium sulfate, followed by filtration, spin-drying, and purification by Combiflash chromatography column to obtain a white solid PA4013 (89 mg), with yield of 51%.

Example 12 PA4014

Synthesis Route:

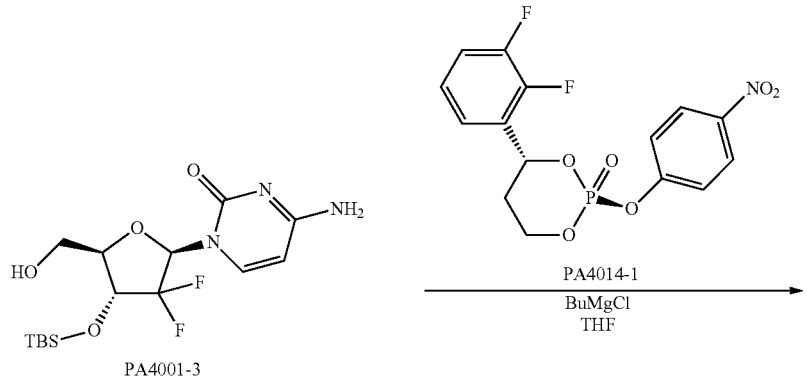

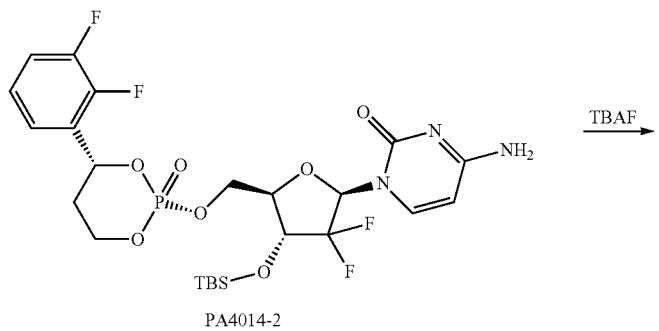

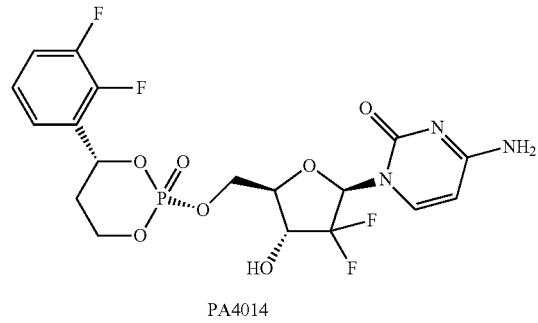

Experimental Section:

Step 1) Synthesis of Compound PA4014-2 dissolving a compound PA4001-3 (300 mg, 0.80 mmol) in anhydrous tetrahydrofuran, slowly adding 1 M tert-butylmagnesium chloride solution (2.8 mL, 2.8 mmol) dropwise in an ice bath, stirring the mixture for 2 hours, adding PA4014-1 (445 mg, 1.2 mmol), stirring the mixture at room temperature overnight, after the reaction was ended, adding saturated ammonium chloride (20 mL) to quench the reaction, followed by extraction with ethyl acetate (3×120 mL), washing with saturated brine, drying over anhydrous sodium sulfate, followed by filtration, spin-drying, and separation and purification by silica gel chromatographic column (DCM:MeOH (V:V)=20:1) to obtain PA4014-2 (310 mg), with yield of 38%.

Step 2) Synthesis of Target Compound PA4014 adding the compound PA4014-2 (310 mg, 0.51 mmol) to THF (5 mL), slowly adding 1 mol/L TBAF solution (0.76 mL) dropwise in an ice bath, stirring the mixture at room temperature for 2 h, after the reaction was ended, adding 100 mL of water, followed by extraction with ethyl acetate (3×100 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4014 (150 mg), with yield of 60%.

Example 13 PA4017

Synthesis Route:

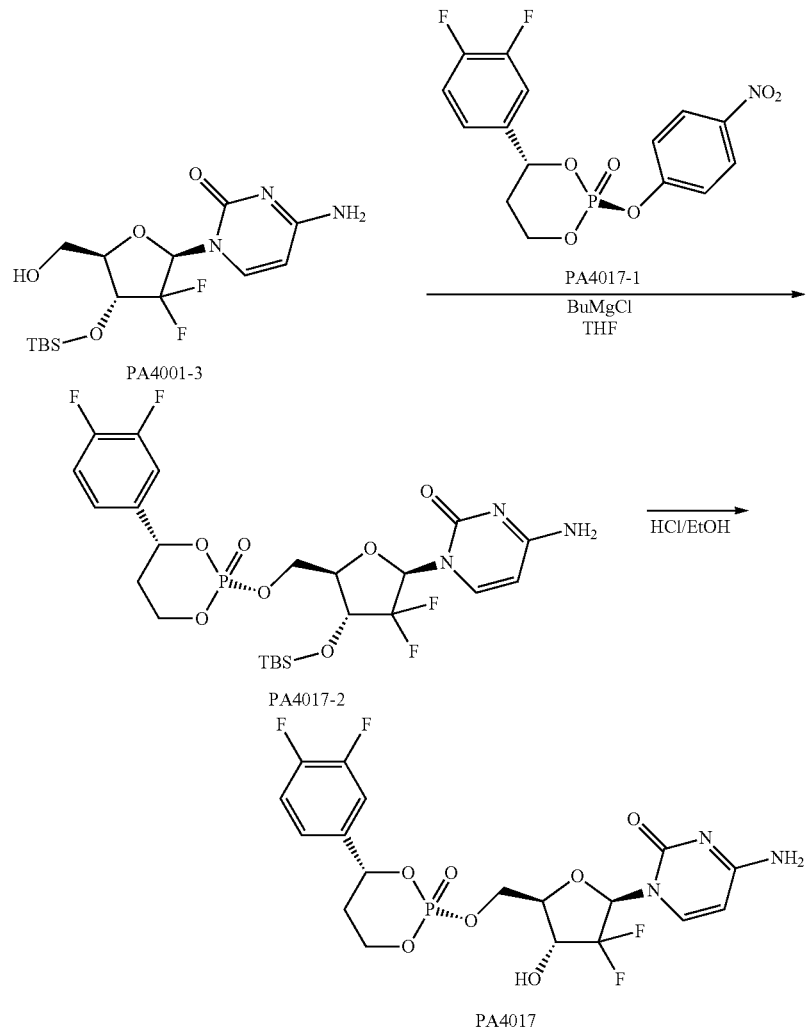

Experimental Section:

Step 1) Synthesis of Compound PA4017-2 dissolving a compound PA4001-3 (377 mg, 1.0 mmol) in tetrahydrofuran (40 mL), slowly adding 1 M tert-butylmagnesium chloride solution (3.5 mL, 3.5 mmol) dropwise in an ice bath, after completing the dropwise addition, stirring the reaction solution at room temperature for 1 hour and then cooling the reaction solution to 0° C., adding PA4017-1 (371 mg, 1.0 mmol), then stirring the reaction solution at room temperature overnight, quenching the reaction with a saturated aqueous ammonium chloride solution (30 mL), followed by extraction with ethyl acetate (3×50 mL), drying over anhydrous Na2SO4, followed by filtration, spin-drying, and separation and purification by silica gel chromatographic column (eluent: DCM:MeOH (V:V)=20.1) to obtain a white solid PA4017-2 (180 mg), with yield of 29%.

Step 2) Synthesis of Target Compound PA4017 dissolving the compound PA4017-2 (180 mg, 0.29 mmol) in 3.6% hydrochloric alcohol solution (10 ml), and carrying out reaction while stirring at room temperature for 2 hours, after the reaction was ended, neutralizing the resultant to make a pH value be neutral with a saturated NaHCO3 solution, after removing ethanol by rotary evaporation, extracting the resultant with ethyl acetate (2×80 mL), washing an organic phase with saturated brine, drying over anhydrous sodium sulfate, followed by filtration, spin-drying, and purification by Combiflash chromatography column to obtain a white solid PA4017 (83 mg), with yield of 58%.

Example 14 PA4018

Synthesis Route:

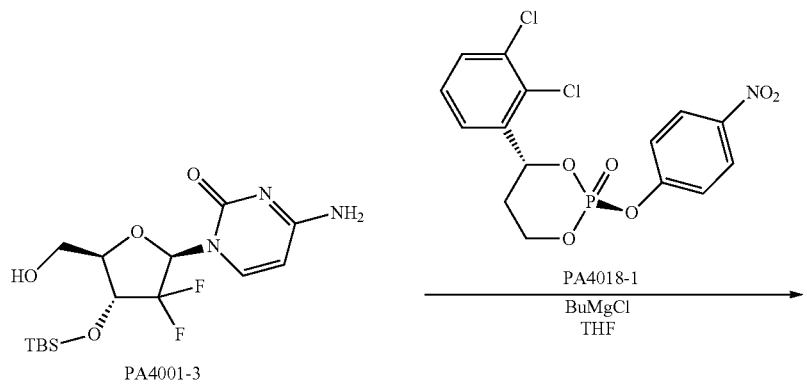

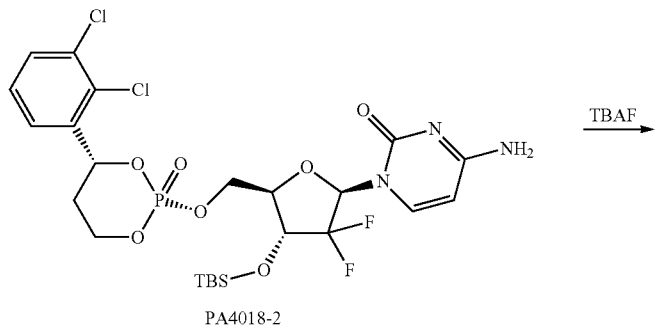

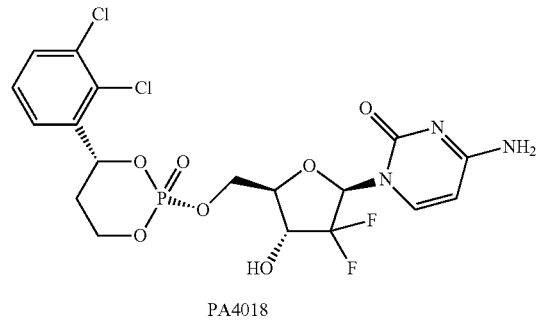

Experimental Section:

Step 1) Synthesis of Compound PA4018-2 dissolving a compound PA4001-3 (200 mg, 0.53 mmol) in anhydrous tetrahydrofuran, slowly adding 1 M tert-butyl-magnesium chloride solution (1.9 mL, 1.9 mmol) dropwise in an ice bath, stirring the mixture for 2 hours, adding PA4018-1 (321 mg, 0.8 mmol), stirring the mixture at room temperature overnight, after the reaction was ended, adding saturated ammonium chloride (20 mL) to quench the reaction, followed by extraction with ethyl acetate (3×100 mL), washing with saturated brine, drying over anhydrous sodium sulfate, followed by filtration, spin-drying, and separation and purification by silica gel chromatographic column (DCM:MeOH (V:V)=20:1) to obtain PA4018-2 (120 mg), with yield of 35%.

Step 2) Synthesis of Target Compound PA4018 adding the compound PA4018-2 (120 mg, 0.19 mmol) to THF (5 mL), slowly adding 1 mol/L TBAF solution (0.28 mL) dropwise in an ice bath, stirring the mixture at room temperature for 2 h, after the reaction was ended, adding 100 mL of water, followed by extraction with ethyl acetate (3×20 mL), washing with saturated brine, drying over anhydrous sodium sulfate, followed by filtration, spin-drying, separation and purification by silica gel chromatographic column (eluent: MeOH:DCM (V:V)=1:20), followed by separation and purification by silica gel chromatographic plate (developing agent: MeOH:DCM (V:V)=1:10), and finally, purification by Combiflash chromatography column, and lyophilization to obtain a pale white solid PA4018 (20 mg), with yield of 200.

Example 15 PA4021

Synthesis Route:

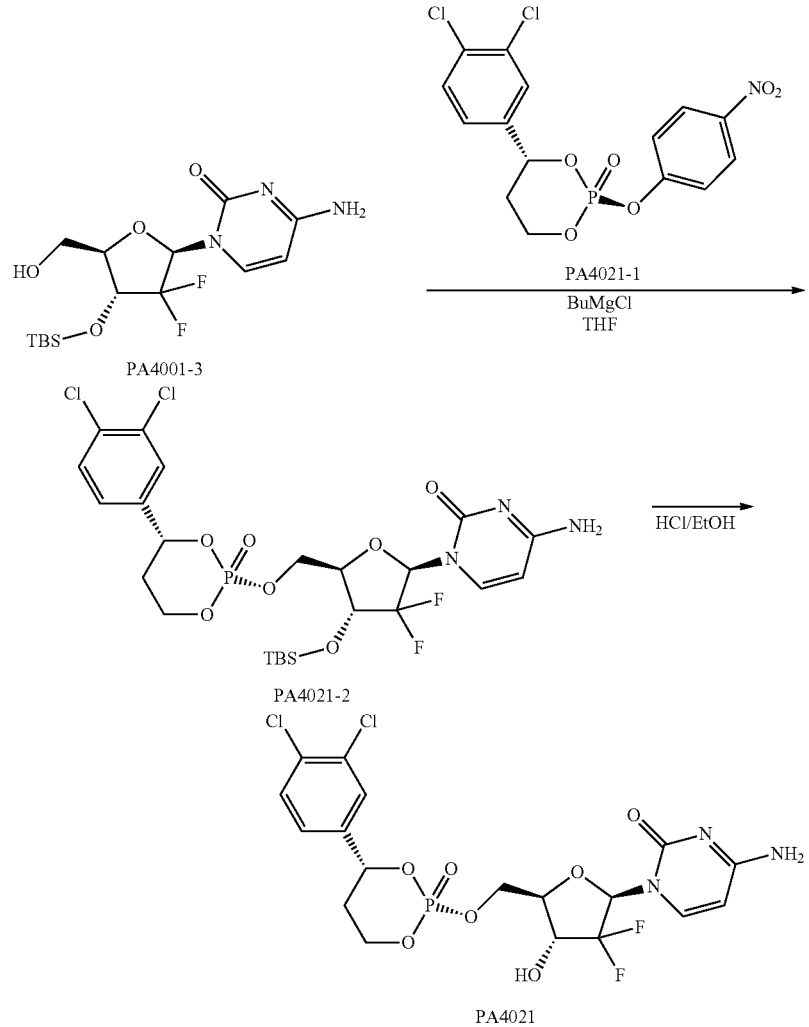

Experimental Section:

Step 1) Synthesis of Compound PA4021-2 dissolving a compound PA4001-3 (377 mg, 1.0 mmol) in tetrahydrofuran (40 mL), slowly adding 1 M tert-butylmagnesium chloride solution (3.5 mL, 3.5 mmol) dropwise in an ice bath, after completing the dropwise addition, stirring thereaction solution at room temperature for 1 hour and then cooling the reaction solution to 0° C., adding PA4021-1 (402 mg, 1.0 mmol), then stirring the reaction solution at room temperature overnight, quenching the reaction with a saturated aqueous ammonium chloride solution (30 mL), followed by extraction with ethyl acetate (3×50 mL), drying over anhydrous Na2SO4, followed by filtration, spin-drying, and separation and purification by silica gel chromatographic column (eluent: DCM:MeOH (V:V)=20:1) to obtain a white solid PA4021-2 (210 mg), with yield of 39.7%.

Step 2) Synthesis of Target Compound PA4021 dissolving the compound PA4021-2 (210 mg, 0.39 mmol) in 3.6% hydrochloric alcohol solution (10 ml), and carrying out reaction while stirring at room temperature for 2 hours, after the reaction was ended, neutralizing the resultant to make a pH value be neutral with a saturated NaHCO3 solution, after removing ethanol by rotary evaporation, extracting the resultant with ethyl acetate (2×60 mL), washing an organic phase with saturated brine, drying over anhydrous sodium sulfate, followed by filtration, spin-drying, and purification by Combiflash chromatography column to obtain a white solid PA4021 (64 mg), with yield of 31%.

TABLE 1

Compounds prepared in each of the examples are as shown in the following Table

| Compound No. | Structure | Molecular Weight |
|---|---|---|
| PA4001 Comparative Example | 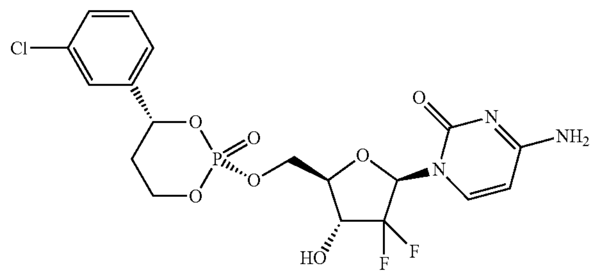 | 493.78 |
| PA4002 | 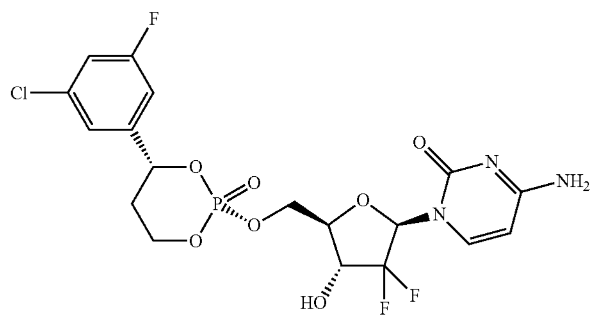 | 511.77 |
| PA4003 | 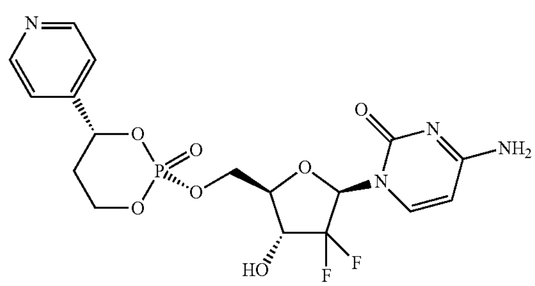 | 460.33 |
| PA4004 | 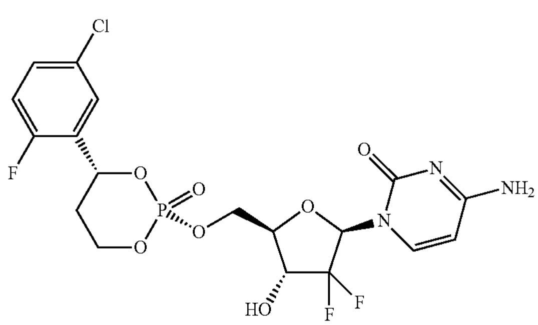 | 511.77 |

TABLE 1-continued

Compounds prepared in each of the examples are as shown in the following Table

| Compound No. | Structure | Molecular Weight |
|---|---|---|
| PA4006 | (3,5-dichlorophenyl cyclic phosphate ester of gemcitabine) | 528.23 |
| PA4008 | (3-chloro-4-fluorophenyl cyclic phosphate ester of gemcitabine) | 511.77 |
| PA4009 | (4-chloro-3-fluorophenyl cyclic phosphate ester of gemcitabine) | 511.77 |
| PA4010 | (3-chloro-2-fluorophenyl cyclic phosphate ester of gemcitabine) | 511.77 |

TABLE 1-continued

Compounds prepared in each of the examples are as shown in the following Table

| Compound No. | Structure | Molecular Weight |
|---|---|---|
| PA4011 | (structure: 2-chloro-5-fluorophenyl cyclic phosphate ester linked to 2'-deoxy-2',2'-difluorocytidine) | 511.77 |
| PA4012 | (structure: 2,5-dichlorophenyl cyclic phosphate ester linked to 2'-deoxy-2',2'-difluorocytidine) | 528.23 |
| PA4013 | (structure: 2,5-difluorophenyl cyclic phosphate ester linked to 2'-deoxy-2',2'-difluorocytidine) | 495.32 |
| PA4014 | (structure: 2,3-difluorophenyl cyclic phosphate ester linked to 2'-deoxy-2',2'-difluorocytidine) | 495.32 |

TABLE 1-continued

Compounds prepared in each of the examples are as shown in the following Table

| Compound No. | Structure | Molecular Weight |
|---|---|---|
| PA4017 | 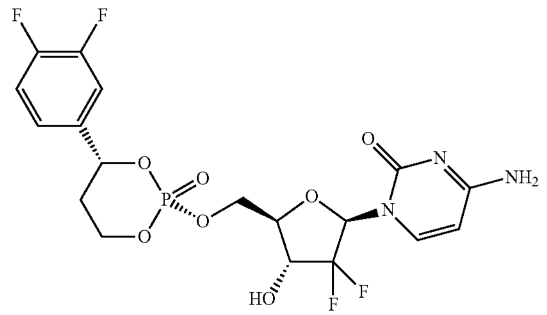 | 495.32 |
| PA4018 | 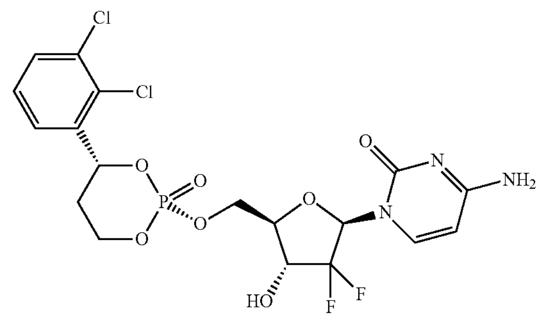 | 528.23 |
| PA4021 | 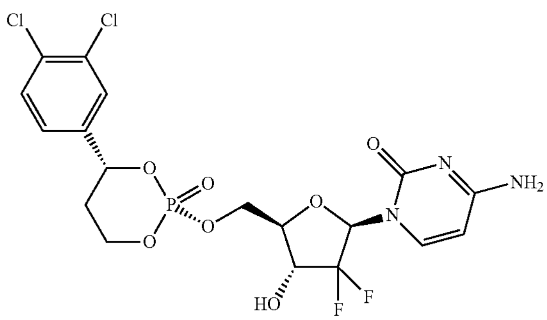 | 528.23 |

TABLE 2

Nuclear magnetism of the compounds prepared in each of the examples is as shown in the following Table

| No. | Nuclear magnetism Data |
|---|---|
| PA4001 Comparative Example | $^1$H NMR (400 MHz, DMSO-$d_6$) δ: 7.50 (t, J = 3.6 Hz, 2H), 7.47-7.36 (m, 4H), 6.19 (d, J = 8.6 Hz, 1H), 5.80-5.65 (m, 2H), 4.63-4.33 (m, 4H), 4.18 (d, J = 8.4 Hz, 1H), 4.03 (dt, J = 8.0, 3.9 Hz, 1H), 2.35-2.13 (m, 2H)ppm. |
| PA4002 | $^1$H NMR (400 MHz, DMSO-$d_6$) δ: 7.68-7.42 (m, 4H), 7.42-7.25 (m, 1H), 6.27 (t, J = 8.5 Hz, 1H), 5.94-5.64 (m, 2H), 4.69-4.36 (m, 4H), 4.31-4.05 (m, 2H), 2.28 (t, J = 19.6 Hz, 2H)ppm. |
| PA4003 | $^1$H NMR (400 MHz, DMSO-$d_6$) δ: 8.75-8.52 (m, 2H), 7.62-7.24 (m, 5H), 6.19 (s, 1H), 5.83-5.68 (m, 2H) 4.66-4.30 (m, 4H), 4.18 (s, 1H), 4.04 (d, J = 4.8 Hz, 1H), 2.31-2.09 (m, 2H) ppm. |
| PA4004 | $^1$H NMR (400 MHz, CDCl$_3$) δ: 7.58 (dd, J = 6.2, 2.6 Hz, 1H), 7.51 (ddd, J = 16.5, 11.3, 6.0 Hz, 2H), 7.44-7.26 (m, 3H), 6.20 (s, 1H), 5.89 (d, J = 11.3 Hz, 1H), 5.71 (t, J = 7.9 Hz, 1H), 4.69-4.31 (m, 4H), 4.16 (d, J = 8.7 Hz, 1H), 4.08-3.94 (m, 1H), 2.47-2.30 (m, 1H), 2.17 (d, J = 14.7 Hz, 1H) ppm. |
| PA4006 | $^1$H NMR (400 MHz, DMSO-$d_6$) δ 7.63 (s, 1H), 7.54-7.48 (m, 3H), 7.42 (s, 2H), 6.50 (s, 1H), 6.20 (s, 1H), 5.73 (dd, J = 13.9, 8.0 Hz, 2H), 4.61-4.31 (m, 4H), 4.16 (s, 1H), 4.04 (dd, J = 8.0, 4.0 Hz, 1H), 2.23 (d, J = 3.2 Hz, 2H)ppm |
| PA4008 | $^1$H NMR (400 MHz, DMSO-$d_6$) δ 7.70-7.64 (m, 1H), 7.54-7.36 (m, 5H), 6.46 (d, J = 6.2 Hz, 1H), 6.20 (s, 1H), 5.77-5.69 (m, 2H), 4.62-4.32 (m, 4H), 4.18 (s, 1H), 4.03 (dt, J = 7.9, 3.9 Hz, 1H), 2.34-2.12 (m, 2H)ppm |

TABLE 2-continued

Nuclear magnetism of the compounds prepared in each of the examples is as shown in the following Table

| No. | Nuclear magnetism Data |
| --- | --- |
| PA4009 | $^1$H NMR (400 MHz, DMSO-d$_6$) δ 7.63 (t, J = 8.0 Hz, 1H), 7.55-7.36 (m, 4H), 7.31 (d, J = 8.0 Hz, 1H), 6.48 (s, 1H), 6.19 (s, 1H), 5.74 (dd, J = 14.5, 8.7 Hz, 2H), 4.63-4.31 (m, 4H), 4.17 (s, 1H), 4.03 (d, J = 4.8 Hz, 1H), 2.23 (d, J = 14.6 Hz, 2H)ppm |
| PA4010 | $^1$H NMR (400 MHz, DMSO-d$_6$) δ 7.64 (t, J = 7.6 Hz, 1H), 7.57-7.38 (m, 4H), 7.29 (t, J = 7.6 Hz, 1H), 6.48 (s, 1H), 6.19 (s, 1H), 5.94 (d, J = 11.1 Hz, 1H), 5.73 (t, J = 10.3 Hz, 1H), 4.62 (d, J = 6.7 Hz, 1H), 4.56-4.42 (m, 1H), 4.37 (dd, J = 6.9, 4.0 Hz, 2H), 4.16 (s, 1H), 4.02 (dd, J = 8.2, 4.0 Hz, 1H), 2.44-2.30 (m, 1H), 2.19 (d, J = 14.8 Hz, 1H)ppm. |
| PA4011 | $^1$H NMR (400 MHz, MeOD) δ 9.58 (s, 1H), 8.95 (s, 1H), 8.54 (d, J = 7.7 Hz, 1H), 8.40 (dd, J = 8.9, 5.1 Hz, 1H), 8.24 (dd, J = 9.5, 3.0 Hz, 1H), 8.17-8.08 (m, 1H), 7.39 (s, 1H), 7.01 (t, J = 8.5 Hz, 1H), 6.72 (dd, J = 20.0, 9.1 Hz, 2H), 5.55-5.41 (m, 1H), 5.37-5.19 (m, 3H), 5.11-4.98 (m, 1H), 4.97-4.88 (m, 1H), 3.09 (ddd, J = 27.1, 18.8, 9.4 Hz, 2H)ppm. |
| PA4012 | $^1$H NMR (400 MHz, DMSO) δ 9.89 (s, 1H), 8.82 (s, 1H), 7.91 (t, 7 = 8.2 Hz, 1H), 7.59 (dt, J = 8.5, 2.9 Hz, 2H), 7.52 (dd, J = 8.6, 2.5 Hz, 1H), 6.69 (s, 1H), 6.19 (t, J = 8.1 Hz, 1H), 6.14 (d, J = 7.9 Hz, 1H), 5.94-5.85 (m, 1H), 4.71-4.60 (m, 1H), 4.55-4.39 (m, 3H), 4.21 (ddd, J = 16.5, 16.0, 9.8 Hz, 2H), 2.38-2.15 (m, 2H)ppm. |
| PA4013 | $^1$H NMR (400 MHz, DMSO) δ 7.47 (d, J = 7.5 Hz, 1H), 7.45-7.24 (m, 5H), 6.48 (d, J = 6.2 Hz, 1H), 6.19 (s, 1H), 5.89 (d, J = 11.4 Hz, 1H), 5.70 (d, J = 7.5 Hz, 1H), 4.62 (s, 1H), 4.48 (s, 1H), 4.38 (dd, J = 6.9, 4.1 Hz, 2H), 4.25-4.07 (m, 1H), 4.07-3.96 (m, 1H), 2.44-2.29 (m, 1H), 2.16 (d, J = 15.1 Hz, 1H)ppm. |
| PA4014 | $^1$H NMR (400 MHz, DMSO) δ 7.48 (dd, J = 15.3, 7.7 Hz, 4H), 7.42-7.32 (m, 1H), 7.32-7.22 (m, 1H), 6.46 (d, J = 6.0 Hz, 1H), 6.19 (t, J = 8.6 Hz, 1H), 6.00-5.90 (m, 1H), 5.72 (d, J = 7.5 Hz, 1H), 4.70-4.58 (m, 1H), 4.56-4.43 (m, 1H), 4.41-4.31 (m, 2H), 4.17 (s, 1H), 4.02 (dt, J = 8.0, 3.9 Hz, 1H), 2.46-2.31 (m, 1H), 2.20 (dd, J = 12.3, 2.4 Hz, 1H)ppm. |
| PA4017 | $^1$H NMR (400 MHz, DMSO) δ 7.59-7.42 (m, 4H), 7.39 (s, 1H), 7.32 (s, 1H), 6.49 (d, J = 5.8 Hz, 1H), 6.19 (s, 1H), 5.74 (dd, J = 9.9, 5.7 Hz, 2H), 4.60-4.34 (m, 4H), 4.21 (s, 1H), 4.02 (s, 1H), 2.30 (d, J = 6.0 Hz, 2H)ppm. |
| PA4018 | $^1$H NMR (400 MHz, DMSO) δ 7.70 (dd, J = 8.0, 1.4 Hz, 1H), 7.61-7.56 (m, 1H), 7.52 (d, J = 7.5 Hz, 1H), 7.46 (d, J = 7.9 Hz, 1H), 7.42 (d, J = 7.5 Hz, 2H), 6.48 (s, 1H), 6.20 (s, 1H), 5.99-5.90 (m, 1H), 5.74 (t, J = 6.3 Hz, 1H), 4.72-4.60 (m, 1H), 4.46 (ddd, J = 19.7, 13.2, 8.8 Hz, 3H), 4.19 (s, 1H), 4.05 (dd, J = 8.2, 3.7 Hz, 1H), 2.29-2.20 (m, 2H)ppm. |
| PA4021 | $^1$H NMR (500 MHz, DMSO) δ 7.68 (dd, J = 9.4, 5.2 Hz, 2H), 7.50 (d, J = 7.6 Hz, 1H), 7.45-7.34 (m, 3H), 6.52-6.42 (m, 1H), 6.25-6.12 (m, 1H), 5.74 (dd, J = 12.1, 9.0 Hz, 2H), 4.60-4.50 (m, 1H), 4.50-4.42 (m, 1H), 4.38 (dd, J = 7.2, 4.1 Hz, 2H), 4.22-4.09 (m, 1H), 4.03 (d, J = 4.0 Hz, 1H), 2.22 (s, 2H). |

Example 16 Evaluation of Human Liver Microsome Metabolism in Viro

Assay Method:

1) Source of Reagent

Human liver microsomes (HLM) were purchased from IVT (In Vitro Technologies), lot number SSP, article number X008070.

Test compounds PA4001, PA4002, PA4003, and PA4004 were synthesized by Zhejiang Palo Alto Pharmaceuticals, Inc., and dissolved in methanol (from Sinopharm Chemical Reagent Co., Ltd.) to prepare a storage solution of a concentration of 25 mM.

2) Reaction Process

Enzymatic reaction was carried out in 100 mM KH2PO4 buffer solution (pH 7.4), the concentration of the test compounds was 25 M, the concentration of human liver microsomes was 2 mg/ml, and NADPH concentration was 2 mM. The reaction was initiated by NADPH finally added, and after reaction for 5 min in a constant-temperature shaking water bath kettle, 1.5 times of volume of methanol containing internal standard (PMPA) was immediately added to terminate the reaction.

3) Sample Processing and Analysis Method

I Sample Pretreatment:

Centrifugation was carried out for 20 minutes at a maximum speed of 13,600 rpm using an Eppendorf tabletop centrifuge. Supernatant was taken, and after being blow-dried by a nitrogen blower, the supernatant was re-dissolved into a mobile phase A (0.1% formic acid v/v aqueous solution).

II Liquid Phase Gradient:

| Time (minute) | Mobile Phase A (0.1% FA in H2O) | Mobile Phase B (acetonitrile) |
| --- | --- | --- |
| 0 | 99 | 1 |
| 1.1 | 90 | 10 |
| 1.5 | 20 | 80 |
| 2.5 | 99 | 1 |

Analytical column: Waters, Acquity UPLC HSS T3 column

Flow rate: 0.5 ml/min

Column temperature: 40° C.

III Mass spectrometry condition

Ion source: electrospray ionization source

Ion mode: positive ion mode

Capillary voltage: 3.0 kV

Temperature: 500° C.

Desolventizing airflow speed: 100 L/h

Scan time: 0.025 s

Cone voltage: 40 V

Collision energy: 18 eV

Q1 (m/z): 358

Q3 (m/z): 152

TABLE 3

Rate of Releasing Monophosphate Product dFdCMP from
Human Liver Microsome Metabolic Compounds in vitro

| Compound | Activation Rate pmol/min/mg HLM |
|---|---|
| PA4001 | 131.0 ± 8.0 |
| PA4002 | 131.9 ± 8.9 |
| PA4003 | 17.9 ± 1.1 |
| PA4004 | 170.5 ± 11.0 |

Results show that: all compounds PA4001, PA4002, PA4003, and PA4004 were activated by human liver microsomes into monophosphate metabolic products in vitro, and different compounds had significant differences in the conversion rate. Unexpectedly, rates of converting PA4002 and PA4004 to dFdCMP were higher than that of PA4001 and far higher than that of PA4003. In the above, conversion rates of PA4002 and PA4004 were about 7.3 times and 9.5 times that of PA4003, respectively, and they were 1.0 time and 1.3 times that of PA4001, respectively (Table 3).

Example 17 Evaluation of Human Liver Microsome Metabolism In Vitro

Assay Method:

1) Source of Reagent

Human liver microsomes (HLM) were purchased from IVT (In Vitro Technologies), article number X008070, lot number IQF.

Test compounds were synthesized by Zhejiang Palo Alto Pharmaceuticals, Inc., and dissolved in methanol (from Sinopharm Chemical Reagent Co., Ltd.) to prepare a storage solution of a concentration of 25 mM.

2) Reaction Process

Enzymatic reaction was carried out in 100 mM KH2PO4 buffer solution (pH 7.4), the concentration of the test compounds was 25 µM, the concentration of human liver microsomes was 2 mg/ml, and NADPH concentration was 2 mM. The reaction was initiated by NADPH finally added, and after reaction for 5 min in a constant-temperature shaking water bath kettle, 1.5 times of volume of methanol containing internal standard (PMPA) was immediately added to terminate the reaction.

3) Sample Processing and Analysis Method

I Sample Pretreatment:

Centrifugation was carried out for 20 minutes at a maximum speed of 13,600 rpm using an Eppendorf tabletop centrifuge. Supernatant was taken, and after being blow-dried by a nitrogen blower, the supernatant was re-dissolved into a mobile phase A (0.1% formic acid v/v aqueous solution).

II Liquid Phase Gradient:

| Time (minute) | Mobile Phase A (0.1% FA in H2O) | Mobile Phase B (acetonitrile) |
|---|---|---|
| 0 | 99 | 1 |
| 1.1 | 90 | 10 |
| 1.5 | 20 | 80 |
| 2.5 | 99 | 1 |

Analytical column: Waters, Acquity UPLC HSS T3 column

Flow rate: 0.5 ml/min

Column temperature: 40° C.

III Mass Spectrometry Condition

Ion source: electrospray ionization source

Ion mode: positive ion mode

Capillary voltage: 3.0 kV

Temperature: A500

Desolventizing airflow speed: 100 L/h

Scan time: 0.025 s

Cone voltage: 40 mV

Collision energy: 18 eV

Q1 (m/z): 358

Q3 (m/z): 152

TABLE 4

Rate of Releasing Monophosphate Product dFdCMP from
Human Liver Microsome Metabolic Compounds in vitro

| Compound | Activation Rate pmol/min/mg HLM |
|---|---|
| PA4004 | 10.98 ± 1.23 |
| PA4006 | 6.92 ± 0.01 |
| PA4008 | 5.45 ± 0.12 |
| PA4009 | 10.45 ± 0.85 |
| PA4010 | 9.56 ± 0.07 |
| PA4011 | 35.28 ± 0.81 |
| PA4012 | 38.95 ± 1.17 |
| PA4013 | 7.23 ± 0.53 |
| PA4014 | 6.49 ± 0.19 |
| PA4017 | 4.32 ± 0.76 |
| PA4018 | 7.62 ± 0.48 |
| PA4021 | 5.25 ± 0.13 |

Results show that: all compounds were activated by human liver microsomes into monophosphate metabolic products in vitro, and different compounds had significant differences in the conversion rate. Unexpectedly, rates of converting PA4012 and PA4011 to dFdCMP were remarkably higher than that of PA4004. In the above, conversion rates of PA4012 and PA4011 are about 3.5 times and 3.2 times that of PA4004, respectively (Table 4).

To sum up, as the compounds of the formula I and the formula II of the present disclosure have higher activity and lower toxic and side effects, they have higher safety.

All documents mentioned in the present disclosure are cited in the present disclosure as if each document was individually cited as reference. Besides, it should be understood that various changes or modifications of the present disclosure could be made by those skilled in the art after reading the above teachings of the present disclosure, and these equivalents also fall within the scope defined by the appended claims of the present disclosure.

What is claimed is:

1. A compound of formula (I), or an optical isomer, a pharmaceutically acceptable salt, a hydrate or a solvate thereof: wherein the compound is selected from the group consisting of:

(I)

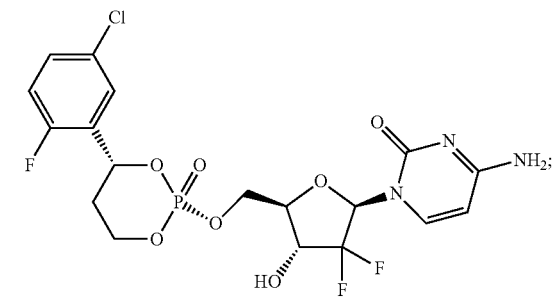

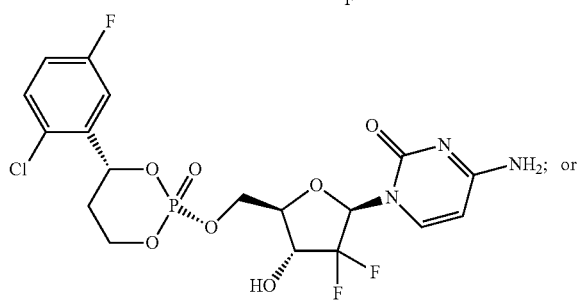

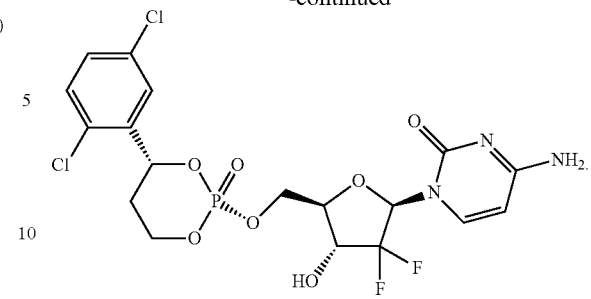

2. A pharmaceutical composition, comprising a therapeutically effective amount of the compound, or an optical isomer, a pharmaceutically acceptable salt, a hydrate or a solvate thereof of claim 1 and a pharmaceutically acceptable adjuvant, a diluent or a carrier.

3. A method for treating a liver cancer in a subject, comprising:
   administering to the subject an effective amount of the compound, or an optical isomer, a pharmaceutically acceptable salt, a hydrate or a solvate thereof of claim 1.

* * * * *